United States Patent
Kon et al.

(10) Patent No.: US 12,268,486 B2
(45) Date of Patent: Apr. 8, 2025

(54) REFLECTIVE PHOTOPLETHYSMOGRAM SENSOR AND BIOLOGICAL INFORMATION MEASUREMENT APPARATUS

(71) Applicant: Konica Minolta, Inc., Tokyo (JP)

(72) Inventors: Shusaku Kon, Hino (JP); Ryo Nakabayashi, Hachioji (JP); Kosuke Ando, Akishima (JP)

(73) Assignee: KONICA MINOLTA, INC., Tokyo (JP)

( * ) Notice: Subject to any disclaimer, the term of this patent is extended or adjusted under 35 U.S.C. 154(b) by 328 days.

(21) Appl. No.: 17/490,699

(22) Filed: Sep. 30, 2021

(65) Prior Publication Data
US 2022/0104718 A1   Apr. 7, 2022

(30) Foreign Application Priority Data

Oct. 2, 2020   (JP) ................................. 2020-167377

(51) Int. Cl.
*A61B 5/024*   (2006.01)

(52) U.S. Cl.
CPC ................................ *A61B 5/02416* (2013.01)

(58) Field of Classification Search
CPC ......................... A61B 5/02416; A61B 5/05427
See application file for complete search history.

(56) References Cited

U.S. PATENT DOCUMENTS

| 8,162,496 B2* | 4/2012 | Kang ................... A61B 5/0059 362/11 |
| 11,331,044 B2* | 5/2022 | Nam ..................... A61B 5/7455 |
| 2002/0111545 A1* | 8/2002 | Lindberg ............... A61B 5/411 600/504 |
| 2004/0012946 A1* | 1/2004 | Parker .................. G02B 6/0021 362/631 |

(Continued)

FOREIGN PATENT DOCUMENTS

| CN | 106308776 A | 1/2017 |
| CN | 107752977 A | 3/2018 |

(Continued)

OTHER PUBLICATIONS

Yuka Maeda, et al., "Position Dependency in Photoplethysmographic sensor Comparison of adjoining PPG signals in Light Sources and Measurement Sites," Journal of Life Support Engineering, 2011, pp. 124-129, vol. 23, No. 3.

(Continued)

*Primary Examiner* — Oommen Jacob

(74) *Attorney, Agent, or Firm* — LUCAS & MERCANTI, LLP

(57) ABSTRACT

Disclosed is a reflective photoplethysmogram sensor comprising: a planar light emitting element and a planar light receiving element. The light emitting element and the light receiving element do not face each other in an up/down direction. The minimum distance h (mm) between at least a pair of the light emitting element and the light receiving element satisfies the following expression (1)

$$(t \times 03.7)^2 \le h \le (t \times 1.3)^2 \qquad \text{Expression (1)}$$

(Continued)

where the minimum distance between the light emitting element and the light receiving element is h (mm), and a thickness of skin (epidermis+dermis) of a human body is t (mm), and the thickness is within the range 0.1 to 4 mm.

9 Claims, 10 Drawing Sheets

(56) References Cited

U.S. PATENT DOCUMENTS

| | | | |
|---|---|---|---|
| 2009/0005661 A1* | 1/2009 | Ozawa | A61B 5/1455 600/322 |
| 2014/0328047 A1* | 11/2014 | Kamee | A61B 1/0684 362/84 |
| 2015/0057511 A1* | 2/2015 | Basu | A61B 5/6826 600/475 |
| 2017/0000350 A1* | 1/2017 | Kwon | A61B 5/0059 |
| 2017/0067778 A1* | 3/2017 | Sugi | G01S 17/88 |
| 2017/0119262 A1* | 5/2017 | Shim | H04W 4/70 |
| 2017/0156651 A1* | 6/2017 | Arias | A61B 5/14552 |
| 2018/0353075 A1* | 12/2018 | Duval | A61B 5/14551 |
| 2020/0294228 A1* | 9/2020 | Hu | A61B 5/7257 |
| 2021/0177353 A1* | 6/2021 | Bhagat | G09G 3/20 |
| 2022/0104718 A1* | 4/2022 | Kon | A61B 5/02416 |

FOREIGN PATENT DOCUMENTS

| | | | |
|---|---|---|---|
| CN | 110461226 A | 11/2019 | |
| JP | 2013-162821 A | 8/2013 | |
| JP | 2017-051340 A | 3/2017 | |
| JP | 6593443 B2 * | 10/2019 | ........... A61B 5/0245 |
| JP | 2020-018430 A | 2/2020 | |
| JP | 2022059660 A * | 4/2022 | ......... A61B 5/02007 |
| WO | 2020/162487 A1 | 8/2020 | |

OTHER PUBLICATIONS

Setsuo Takatani, "Theoretical Basis, Current Status and Future Perspectives of Optical Oximetry," Japanese Journal of Optics, Japan, Oct. 10, 2001, pp. 644-650, vol. 30, No. 10.
Office Action for dated May 4, 2023 for corresponding Chinese Application No. 202111140196.0, with English translation.
Office Action for dated Dec. 12, 2023 for corresponding Japanese Application No. 2020-167377, with English translation.
JPO, Japanese Office Action mailed Apr. 16, 2024 for the related Japanese application No. 2020-167377, with English Machine translation, 6 pages.
Decision of Refusal, mailed on Sep. 3, 2024, issued for the corresponding Japanese Patent Application No. 2020-167377, 3 pages, with English Translation.
Decision of Dismissal of Amendment, mailed on Sep. 3, 2024, issued for the corresponding Japanese Patent Application No. 2020-167377, 6 pages, with English Translation.

* cited by examiner

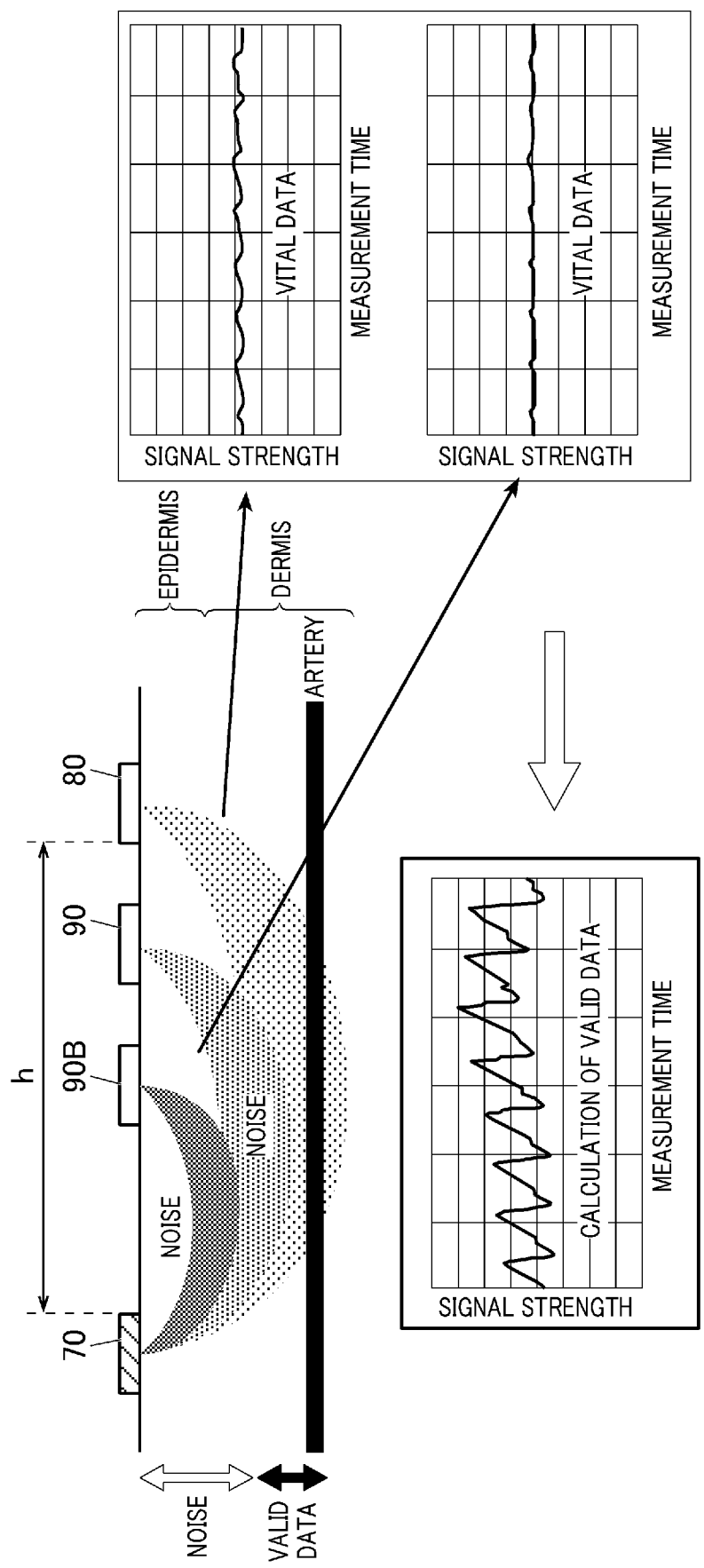

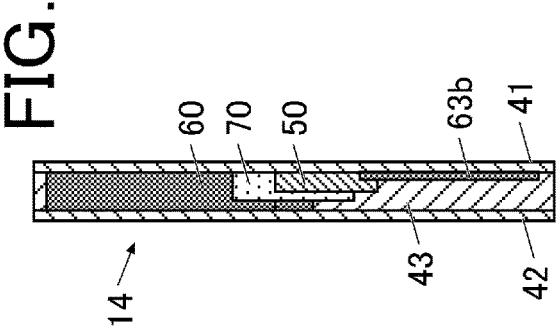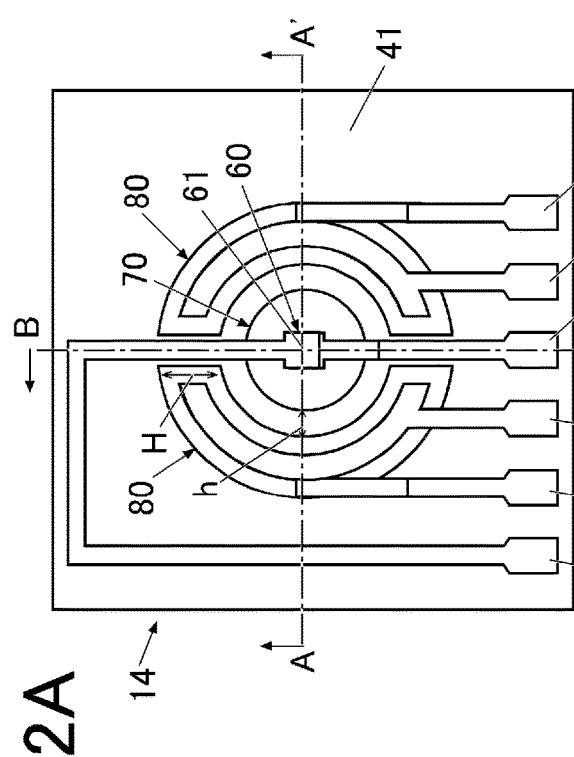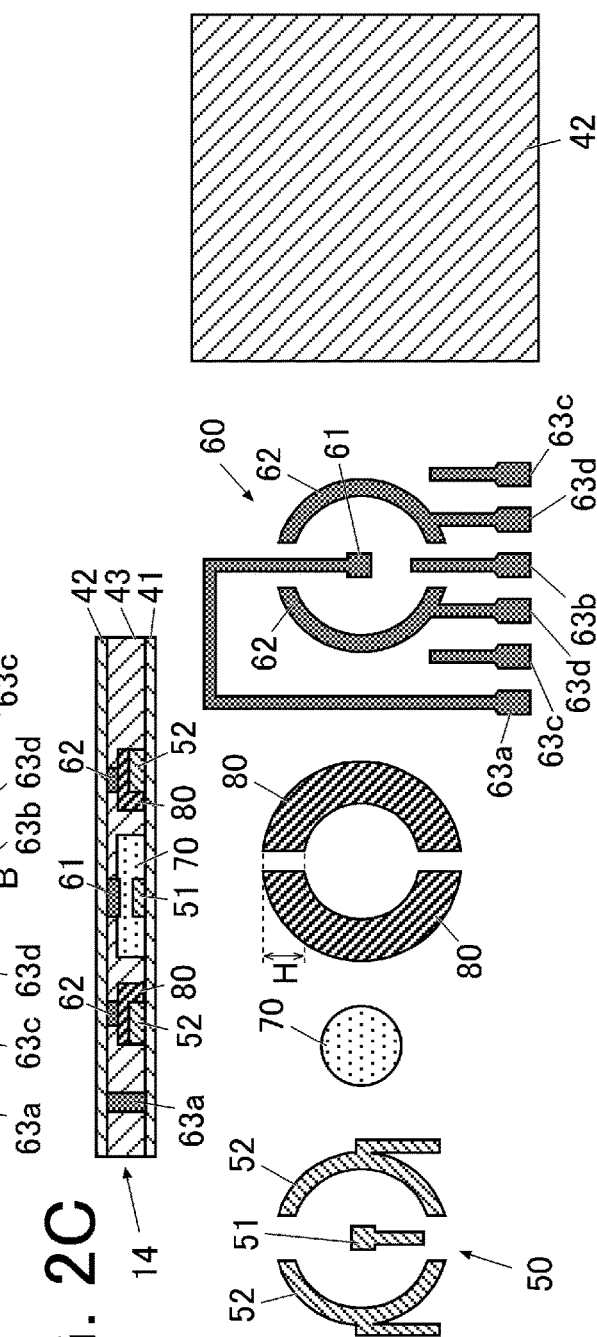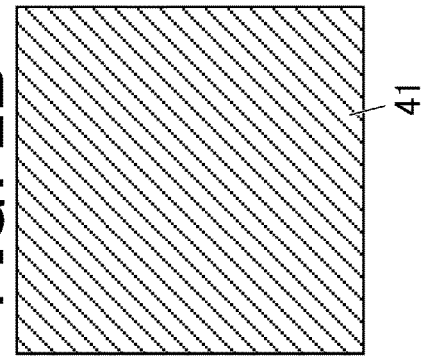

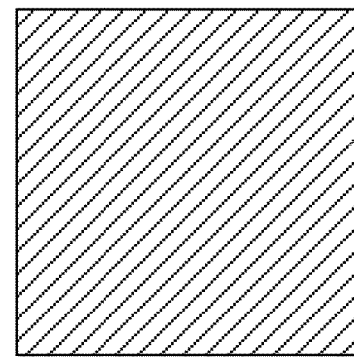
FIG. 7D
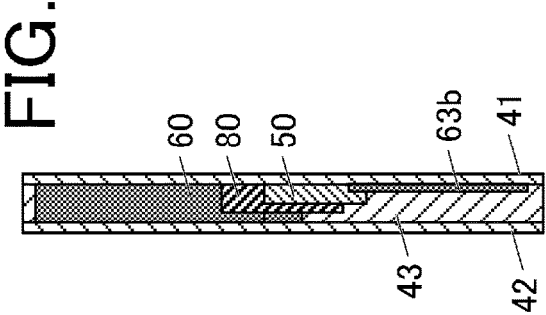
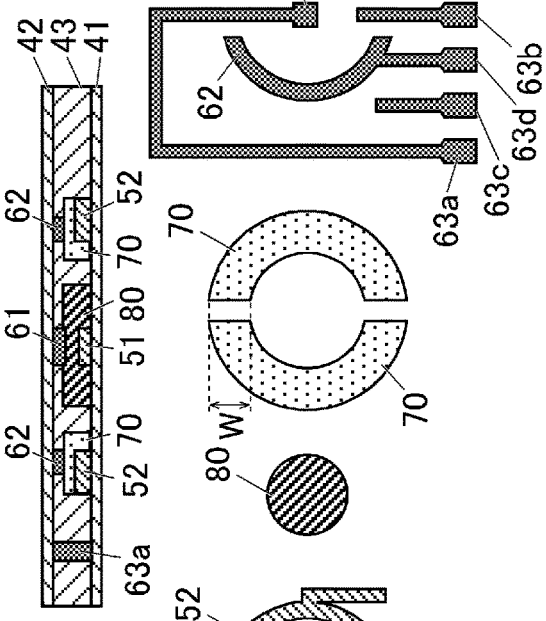
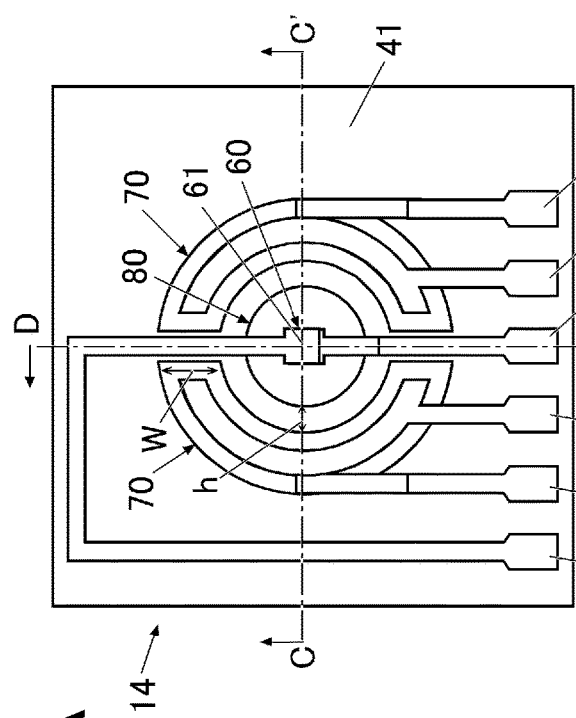
FIG. 7A
FIG. 7C
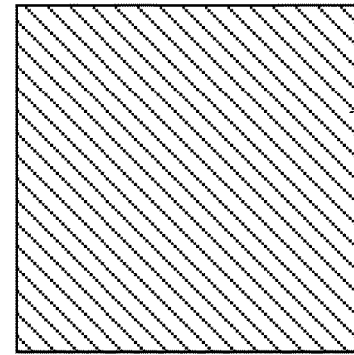
FIG. 7B

REFLECTIVE PHOTOPLETHYSMOGRAM SENSOR AND BIOLOGICAL INFORMATION MEASUREMENT APPARATUS

CROSS-REFERENCE TO RELATED APPLICATIONS

The entire disclosure of Japanese Patent Application No. 2020-167377 filed on Oct. 2, 2020 is incorporated herein by reference in its entirety.

BACKGROUND

Technological Field

The present invention relates to a reflective photoplethysmogram sensor and a biological information measurement apparatus provided with the same, and in particular relates to, for example, a reflective photoplethysmogram sensor that can establish both wearability and measurement accuracy by the performance of an optimal design in accordance with, for example, skin thickness at a measurement site.

Description of the Related Art

Services that allow a person to have their health state checked or undergo medical care without the person going to a hospital are being active considered. Attention is being given to photoplethysmography (PPG), which enables vital data (biological information) to be obtained non-invasively. PPG is widely used in a conventional pulse oximeter, and recently is being applied to activity meters and is being used in systems that constantly record a pulse.

The former pulse oximeter requires high accuracy in detecting a pulse wave in order to use the pulse wave to measure the difference between the absorbance of red light and the absorbance of infrared light, whereas the latter activity meter may have a comparatively low accuracy and uses green light because green light has little impact on position deviation and has superior convenience (refer to Yuka Maeda, et. al., Position Dependency in Photoplethysmographic sensor-Comparison of adjoining PPG signals in Light Sources and Measurement Sites-, Journal of Life Support Engineering, Vol. 23, No. 3, 2011, pages 124-129).

Note that, in the present specification, "vital data" refers to any biological information such as, for example, a pulse wave, a heart rate, an electrocardiogram, a blood oxygen concentration, a respiration rate, or a blood pressure.

Due to the rise in health awareness in recent years, a trend to constantly obtain vital data through a wearable device and connect this vital data to precautionary or disease alerts is accelerating Realizing these requires achieving both accuracy and wearability, and although obtaining a pulse wave in addition to a pulse with high accuracy as medical data is required, currently most systems use the transmission method which involves inserting a fingertip and is used in conventional pulse oximeters.

However, in the case of the transmission method, the system needs to be worn on a terminal site such as a fingertip or base of a finger, and is not suited to constant measurement.

In contrast, most activity meters are of a reflective type that uses green light, and are mainly worn on the wrist (on the side of the back of the hand), but it is difficult to detect a highly accurate pulse wave at this site. High accuracy is not needed if only a pulse is measured.

Light with a wavelength longer than red is needed in order to cause the light to be incident within a living body. It is also desirable to detect an artery which is deep in a living body (an artery is what generates a pulse wave), and it is particularly desirable to detect arterioles within dermis.

In the case of the reflective type, because the light source and the sensor are on the same surface, in order for light to reach the sensor, only light which scatters within the living body and returns back (from the side opposite to the emission direction of the light) is a target of detection. At this time, it is necessary to separate the light source and sensor by a certain level in order to reliably detect light that has passed through an arteriole.

In the case of the reflective type, it is also desirable to dispose the light source and the sensor on the same surface, and the technology described in US Patent Application Publication No. 2017/0156651 is disclosed as background art. This combines an organic EL diode and an organic PD, and thus is suitable for improving close contact and improving wearability. In relation to the distance between a light source and a sensor, the Japanese Journal of Optics (country of publication: Japan, publication date: Oct. 10, 2001, Vol. 30, No. 10, pp. 644-650) discloses a technique, and describes increasing the sensitivity by increasing the distance.

SUMMARY

However, because skin thicknesses and sizes that permit wearing both differ in accordance with individual differences and sites where measurement is to be performed, there is a problem in that it is necessary to perform optimal design for each measurement site.

The abovementioned documents do not indicate what level of distance is desirable.

The present invention is made in light of the abovementioned problem and circumstances, and an object is to provide a reflective photoplethysmogram sensor and a biological information measurement apparatus that can achieve both wearability and measurement accuracy by performing optimal design in accordance with, for example, the thickness of skin at a measurement site.

To achieve at least one of the abovementioned objects, the inventors arrived at the present invention by finding that, in the process of considering causes for the abovementioned problem, it is possible to provide, for example, a reflective photoplethysmogram sensor that can achieve both wearability and measurement accuracy by prescribing the relationship between skin thickness and the distance between the light emitting element and the light receiving element to be within a specific range.

In other words, one of the abovementioned objects, according to an aspect of the present invention, is solved by the following means.

To achieve at least one of the abovementioned objects, according to another aspect of the present invention, a reflective photoplethysmogram sensor reflecting one aspect of the present invention comprises: a planar light emitting element and a planar light receiving element, wherein the light emitting element and the light receiving element do not face each other in an up/down direction, and a minimum distance h (mm) between at least a pair of the light emitting element and the light receiving element satisfies the following expression (1)

$$(t \times 0.7)^2 \leq h \leq (t \times 1.3)^2$$  Expression (1):

where the minimum distance between the light emitting element and the light receiving element is h (mm), and a thickness of skin (epidermis+dermis) of a human body is t (mm), and the thickness is within the range 0.1 to 4 mm.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 1 is a schematic view for describing the relationship between skin thickness and the minimum distance between a light emitting element and a light receiving element in a reflective photoplethysmogram sensor;

FIG. 2A through 2D are schematic views for describing the disposition of a light emitting element, a light receiving element, and the like that make up a reflective photoplethysmogram sensor according to a first embodiment;

FIG. 7A through 7D are schematic views for describing the disposition of a light emitting element, a light receiving element, and the like that make up a reflective photoplethysmogram sensor according to a second embodiment;

DETAILED DESCRIPTION OF THE EMBODIMENTS

Figure 3:
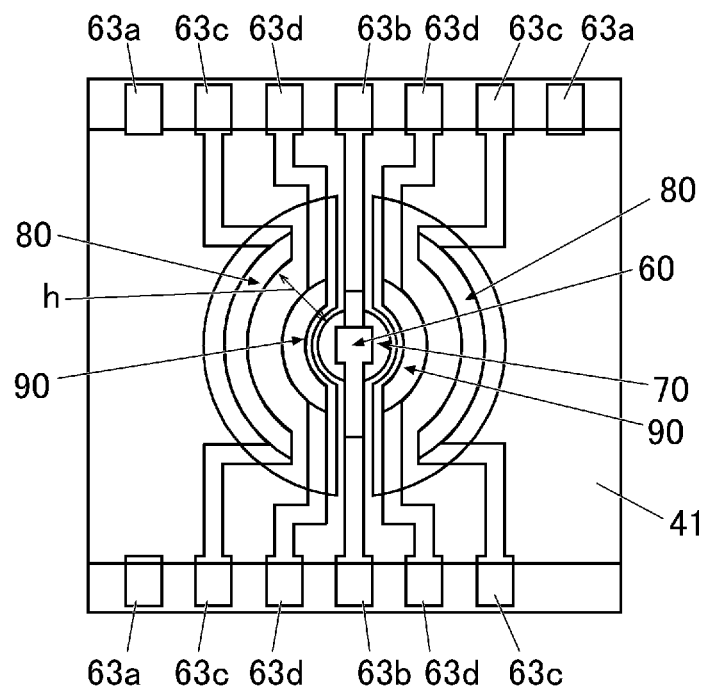
FIG. 3 is a view that illustrates a variation of the disposition or the like in FIG. 2.

A reflective photoplethysmogram sensor according to the present invention is provided with a planar light emitting element and a planar light receiving element, wherein the light emitting element and the light receiving element do not face each other in an up/down direction, and when a minimum distance between the light emitting element and the light receiving element is h (mm), the thickness of skin (epidermis+dermis) of a human body is t (mm), and the thickness is within the range 0.1-4 mm, the minimum distance h (mm) between at least one group of the light emitting element and the light receiving element satisfies the following expression (1).

$$(t \times 0.7)^2 \leq h \leq (t \times 1.3)^2 \qquad \text{Expression (1):}$$

This feature is a technical feature common or corresponding to the following embodiments.

As a specific aspect of the present invention, that the minimum distance between the light emitting element and the light receiving element is within the range of 2-25 mm is desirable from the viewpoint of improving measurement accuracy.

It is desirable that the light emitting element is an organic EL diode from the viewpoints of having good wearability due to being flexible, and being able to reduce wavelength variation or luminance variation.

It is desirable that the light receiving element is an organic photodiode from a viewpoint similar to that described above.

Providing a plurality of the light emitting element and having the light emitting elements be disposed on approximately concentric circles centered on the center point of the light receiving element can improve robustness with respect to position deviation. In particular, in a case where an organic EL diode is used as a light emitting element, because it is possible to reduce the amount of light per unit area due to an organic EL diode being a surface light source, a low-temperature burn is less likely in comparison to a case where an LED which is a point light source is used.

Providing a plurality of the light emitting element, having at least two of the plurality of light emitting elements radiate light of the same wavelength, and being able to separately emit light from the plurality of light emitting elements enables data processing on the basis of light emitted from the plurality of light emitting elements, and, as a result, enables valid data resulting from subtracting noise to be calculated, and is desirable from a viewpoint of improving measurement accuracy.

Processing information or data obtained on the basis of light respectively emitted from, among the plurality of the light emitting element, a light emitting element disposed at a position near the light receiving element and a light emitting element disposed at a position farther away from the light receiving element than this light emitting element enables valid data resulting from subtracting noise to be calculated, and is desirable from a viewpoint of improving measurement accuracy.

Providing a plurality of the light receiving element and having the light emitting elements be disposed on approximately concentric circles centered on the center point of the light receiving element can improve robustness with respect to position deviation.

Processing information or data obtained on the basis of light respectively received by, among the plurality of the light receiving element, a light receiving element disposed at a position near the light emitting element and a light receiving element disposed at a position farther away from the light emitting element than this light receiving element enables valid data resulting from subtracting noise to be calculated, and is desirable from a viewpoint of improving measurement accuracy.

There being a plurality of different minimum distances between the light emitting element and the light receiving element, and selecting the light emitting element and the light receiving element having a minimum distance suitable for sensing enables valid data resulting from subtracting noise to be calculated, and is desirable from a viewpoint of improving measurement accuracy.

The abovementioned reflective photoplethysmogram sensor can be suitably used in various types of biological information measurement apparatuses.

Description is given below regarding the present invention, components thereof, and forms and aspects for working the present invention. Note that, in the present application, "-" is used to mean that numbers written therebefore and thereafter are included as a lower limit and an upper limit, respectively.

1. [Outline of Reflective Photoplethysmogram Sensor According to the Present Invention]

A reflective photoplethysmogram sensor according to the present invention is provided with a planar light emitting element and a planar light receiving element, wherein the light emitting element and the light receiving element do not face each other in an up/down direction, and when a minimum distance between the light emitting element and the light receiving element is h (mm), the thickness of skin (epidermis+dermis) of a human body is t (mm), and the thickness is within the range 0.1-4 mm, the minimum distance h (mm) between at least one group of the light emitting element and the light receiving element satisfies the following expression (1).

$$(t\times 0.7)^2 \leq h \leq (t\times 1.3)^2 \qquad \text{Expression (1)}$$

In addition, the minimum distance between the light emitting element and the light receiving element being within the range of 2-25 mm is desirable from the viewpoint of improving measurement accuracy, and, in particular in light of the size of a device, an upper limit for the minimum distance being less than or equal to 17.5 mm is desirable, and being less than or equal to 10 mm is most desirable.

<Functionality of Reflective Photoplethysmogram Sensor>

A reflective photoplethysmogram sensor according to the present invention irradiates light onto a measured part of biological tissue in accordance with a light emitting element such as a light emitting diode as a light source, detects light reflected by the measured part of the biological tissue in accordance with a light receiving element such as a photodiode as a light detection sensor, and, on the basis of a detected signal, measures change such as a plethysmogram of the biological tissue.

For example, light emitted from the light emitting element penetrates epidermis and reaches a blood vessel thereunder. Light that reaches the blood vessel is absorbed or reflected by blood flowing through the blood vessel, or penetrates the blood.

Among this, light scattered by vascular tissue or blood is incident on the light receiving element. Accordingly, the light receiving element outputs a photocurrent in accordance with the amount of incident light. Here, the blood vessel repeatedly expands and contracts with the same period as a heartbeat. Accordingly, because the amount of reflection of the light increases and decreases with the same period as the period of expansion and contraction of the blood vessel, change in the photocurrent outputted from the light receiving element indicates the change of the volume of the blood vessel.

In addition, a reflective photoplethysmogram sensor according to the present invention can also be applied to a sensor for detecting the oxygen saturation of arterial blood. Hemoglobin in blood has different absorbances for red light and infrared light in accordance with whether or not the hemoglobin is bonded to oxygen. Accordingly, it is possible to detect the oxygen saturation by preparing a plurality of element groups that are caused to have different emission wavelengths and received wavelengths, such as with elements for emitting and receiving red light and elements for emitting and receiving infrared light, and measuring and analyzing the light reflected for each group.

Note that "blood vessel" means an artery.

Note that a "plethysmogram" means a waveform for when pressure change in the blood vessel due to the pulsation causes a change in volume of the blood vessel, enables change of the blood vessel to be directly understood.

In addition, a "photoplethysmogram" is a waveform detected by using the transmission or reflection of light by blood in order to detect a plethysmogram.

<Method of Calculating Oxygen Saturation>

Generally, the abovementioned reflective photoplethysmogram sensor (a pulse oximeter) is used in order to measure oxygen saturation in blood. A pulse oximeter irradiates a finger with light with two wavelengths included in a wavelength range of red to near-infrared, and measures the transmittance or reflectance for this light.

Specifically, blood hemoglobin (Hb) is present in four states: oxygenated hemoglobin ($O_2Hb$), reduced hemoglobin (HHb), methemoglobin (MetHb), and carboxyhemoglobin (COHb). MetHb and COHb are abnormal hemoglobin that increase due to methemoglobinemia or carbon monoxide poisoning. Accordingly, oxygen saturation is ordinarily determined in accordance with the ratio of $O_2Hb$ to $O_2Hb+$HHb. In a case where red light is caused to penetrate hemoglobin (Hb), the absorbance of red light by HHb is remarkably greater than the absorbance of red light by $O_2Hb$, and greatly changes in accordance with the wavelength of red light. In addition, in a case where near-infrared light is caused to penetrate hemoglobin (Hb), the absorbance of near-infrared light by HHb is slightly less than the absorbance of near-infrared light by $O_2Hb$. Accordingly, the ratio R between the absorbance of red light and the absorbance of near-infrared light (absorbance of red light/absorbance of near-infrared light) for hemoglobin changes in accordance with oxygen saturation which is the ratio between $O_2Hb$ and $O_2Hb+$HHb in blood.

In addition, arterial blood, venous blood, tissue, and bone are present near a measurement site such as a finger, wrist, the back of an arm, the chest, or the abdomen, and these affect the absorbance of infrared light and the absorbance of near-infrared light. Of these, arterial blood contributes to a change in volume for a plethysmogram. Letting the absorbance of a pulse wave portion be AC, and the absorbance for an arterial blood non-pulsation portion, venous blood, tissue, and bone be DC, letting the AC component of the absorbance of red light having a wavelength of 660 nm, for example, be AC 660 and the DC component be DC 660, and letting the AC component of the absorbance of near-infrared light having a wavelength of 940 nm, for example, be AC 940 and the DC component be DC 940, the ratio R between the absorbance of red light and the absorbance of near-infrared light (absorbance of red light/absorbance of near-infrared light) is represented by the following Expression (I).

[Math. 1]

$$R = \frac{\text{red light absorbance}}{\text{near-infrared light absorbance}} = \frac{AC660/DC660}{AC940/DC940} \qquad \text{Expression (I)}$$

It is possible to obtain the blood oxygen saturation on the basis of an R value calculated from the abovementioned Expression (I), and a calibration curve indicating the relationship between R values empirically obtained in advance and percutaneous arterial oxygen saturation ($SpO_2$).

In addition, ordinarily, when absorbance is measured by irradiating red light and near-infrared light onto a finger, wrist (for example, ulna side or radius side), back of an arm, chest, or abdomen, the change over time of the absorbance is measured as a waveform that reflects the pulse wave.

Accordingly, the AC component of absorbance can be specified by calculating the difference between the maximum value and minimum value of the change over time of the absorbance, and the DC component of the absorbance can be specified by calculating an average of the change over time of the absorbance. In examples described below, values calculated in this manner are written as "AC/DC".

<Distance Between Light Emitting Element and Light Receiving Element>

The light emitting element and light receiving element according to the present invention do not face each other in an up/down direction, and when a minimum distance between the light emitting element and the light receiving element is h (mm), the thickness of skin (epidermis+dermis) of a human body is t (mm), and the thickness is within the range 0.1-4 mm, the minimum distance h (mm) between at least one group of the light emitting element and the light receiving element satisfies the following Expression (1).

$$(t \times 0.7)^2 \leq h \leq (t \times 1.3)^2 \qquad \text{Expression (1):}$$

Note that the abovementioned Expression (1) means that the minimum distance between the light emitting element and the light receiving element is a length "within the range of the square of a numerical value for the skin thickness ±30%". In addition, in the abovementioned Expression (1), h and t represent purely numerical values.

"the light emitting element and the light receiving element . . . do not face each other (in an up/down direction)" means that the light emitting element and the light receiving element are not disposed so as to overlappingly face each other in the up/down direction, and are arranged side by side in a planar direction.

FIG. 1 is a schematic view for describing the relationship between skin thickness as the minimum distance between the light emitting element and the light receiving element.

In the present invention, "skin thickness of a human body" refers to the total thickness of the thickness of the epidermis and the thickness of the dermis of a human body, it is assumed that the skin thickness is within a range of 0.1-4 mm.

In addition, in the present invention, "minimum distance between the light emitting element and the light receiving element" refers to a minimum distance h (mm) from a side edge on a light emitting element 80 side of a light receiving element 70 to a side edge on a light receiving element 70 side of a light emitting element 80, in a side cross-sectional view as illustrated in FIG. 1.

FIG. 1 takes as an example a case in which a plurality of light emitting elements 80, 90, and 90B are provided with respect to one light receiving element 70, where the minimum distance h (mm) between the light receiving element 70 and the light emitting element 80 is within a range that satisfies Expression (1).

Note that it is assumed that the minimum distance between the light receiving element 70 and the light emitting element 90 and the minimum distance between the light receiving element 70 and the light emitting element 90B are not within a range that satisfies Expression (1).

Accordingly, although description is given below, biological information (vital data) obtained on the basis of light emitted from the light emitting elements 90 and 90B which do not satisfy the range for the minimum distance prescribed in the present invention includes noise. From vital data obtained on the basis of light emitted from the light emitting element 80 which satisfies the range for the minimum distance, it is possible to calculate valid vital data by subtracting the vital data that includes noise.

1.1 [Disposition of Light Emitting Element and Light Receiving Element]

The disposition of a light emitting element and a light receiving element according to the present invention is not limited as long as the abovementioned condition is satisfied, but a desirable example of disposition is described below.

A first embodiment described below is a case in which a plurality of light emitting elements are disposed on approximately concentric circles centered on the center point of a light receiving element, and a second embodiment described below is a case in which a plurality of light receiving elements are disposed in approximately concentric circles centered on the center point of a light emitting element.

Here, "on approximately concentric circles" refers to the difference of the distance (radius) between the center point of a light receiving element and the center point of each light emitting element being within 10%, desirably within 5%, more desirably within 3%, and includes the center points being the same.

The "center point of a light receiving element" refers to the geometric center for the shape of the light receiving element in a plan view for the light receiving element. The "center point of a light emitting element" refers to the geometric center for the shape of the light emitting element in a plan view for the light receiving element.

Note that "plan view" refers to viewing the reflective photoplethysmogram sensor from a normal direction with respect to the top surface of a substrate 41.

First Embodiment

FIGS. 2A through 2D are schematic views for describing the disposition of a light emitting element, a light receiving element, and the like that make up a reflective photoplethysmogram sensor. FIG. 2A is a plan view, FIG. 2B is a plan view that decomposes each member, FIG. 2C is a cross-sectional view taken along arrows A-A', and FIG. 2D is a cross-sectional view taken along arrows B-B'.

As illustrated in FIGS. 2A through 2D, for a detector 14, a plurality of let-out electrode sections 63*a*, 63*b*, 63*c*, and 63*d* for an optically transparent first electrode (positive electrode) 50 and an optically transparent second electrode (negative electrode) 60 are formed on a translucent substrate 41.

As the translucent substrate 41, it is desirable to use a substrate for which total light transmittance is greater than or equal to 70%, more desirably greater than or equal to 80%, and particularly desirably greater than or equal to 90%. The total light reflectance can be measured in accordance with JIS K 7375:2008 "Plastics—Determination of total luminous transmittance and reflectance". In addition, as an opaque substrate (light reflective substrate), for example, a metal plate made of aluminum, stainless steel, or the like, a film, an opaque resin substrate, or a substrate made of a ceramic may be given.

In FIG. 2B, the first electrode 50 is provide with a first central electrode section 51 formed at the center of the translucent substrate 41, and first circumferential electrode sections 52 and 52 disposed on a left side and a right side of concentric circles centered on the first central electrode section 51.

The first circumferential electrode sections 52 and 52 each form an arc shape in a plan view, and are uninterruptedly formed so that the first circumferential electrode sections 52 and 52 are not mutually contiguous with each other.

In addition, the first central electrode section 51 is formed extending on the let-out electrode section 63*b* side. Furthermore, the two first circumferential electrode sections 52 and 52 are also formed extending on the let-out electrode section 63*c* side.

The let-out electrode sections 63*a*, 63*b*, 63*c*, and 63*d* are formed on the translucent substrate 41, and are made to be wiring that is let out to a side edge of the translucent substrate 41.

The light receiving element 70 is formed above the first central electrode section 51 in the first electrode 50, so as to cover the first central electrode section 51. The light receiving element 70 forms a circular shape in a plan view.

As the light receiving element 70, it is desirable to use planar organic photovoltaics (OPV) or an organic photodiode (OPD), and in particular using an organic photodiode is desirable from the viewpoints of having good wearability due to being flexible, and being able to reduce wavelength variation or luminance variation. Description is given below regarding details of organic photovoltaics and organic photodiodes.

In addition, light emitting elements 80 and 80 are respectively formed, over the left and right first circumferential electrode sections 52 and 52 in the first electrode 50, so as to cover the first circumferential electrode sections 52 and 52. The light emitting elements 80 and 80 respectively form an arc shape in a plan view along the first circumferential electrode sections 52 and 52, and the light emitting elements 80 and 80 are uninterruptedly formed so as to not be mutually contiguous with each other.

In this manner, the two light emitting elements 80 and 80 formed on the first circumferential electrode sections 52 and 52 are disposed on concentric circles centered on the center point of the light receiving element 70.

In addition, it is desirable that a minimum width H in the plan view for a light emitting element 80 is approximately 5 mm.

Figure 6:
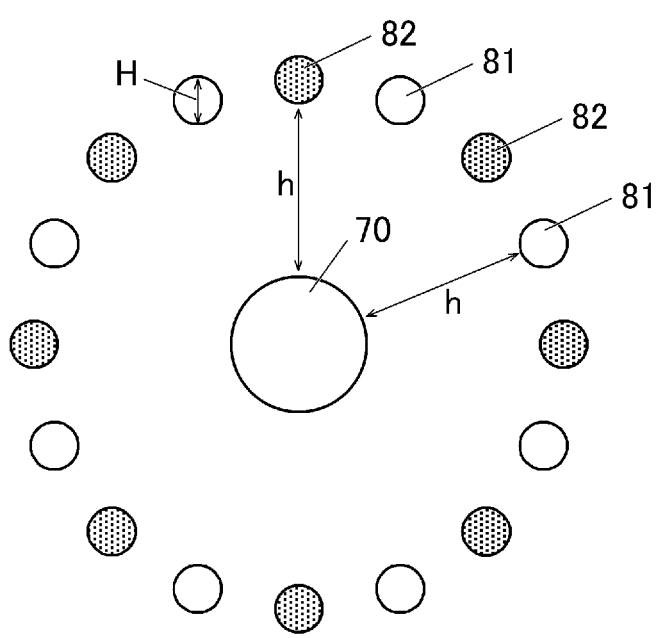
FIG. 6 is a view that illustrates a variation of the disposition or the like in FIG. 2.

Here, the "minimum width H" in the plan view for a light emitting element 80 refers to, in a case where the light emitting element 80 has an arc shape in a plan view, the length of a line orthogonal to respective tangents drawn for the outer peripheral surface and the inner peripheral surface of the arc shape. Note that, in a case where a light emitting elements 81 and 82 have a circular shape in a plan view as illustrated in FIG. 6 described below, the "minimum width H" refers to the diameter of the circle.

Here, the minimum distance h (mm) between at least a group of a light emitting element 80 and a light receiving element 70 satisfies the abovementioned Expression (1). The "minimum distance h" between the light emitting element 80 and the light receiving element 70 refers to, as described above, a minimum distance h (mm) from a side edge on the light emitting element 80 side of the light receiving element 70 to a side edge on the light receiving element 70 side of the light emitting element 80, in a side cross-sectional view as illustrated in FIG. 1. In FIG. 2, because the light receiving element 70 has a circular shape in a plan view and the light emitting element 80 has an arc shape in a plan view, the minimum distance h is between the outer peripheral surface of the light receiving element 70 and the inner peripheral surface of the light emitting element 80. Note that, as indicated in FIG. 6 described below, in a case where the light emitting element 80 has a circular shape in a plan view, the minimum distance is between the outer peripheral surface of the light receiving element 70 and the outer peripheral surfaces of the light emitting elements 81 and 82.

As the light emitting element 80, it is desirable to use a light emitting diode (LED) or an organic EL diode (OLED), and in particular using an organic EL diode is desirable from the viewpoint of being able to reduce wavelength variation or luminance variation.

In addition, for the two light emitting elements 80 and 80, it is desirable to use light emitting elements that both emit light of the same wavelength.

A second electrode 60 is also formed on the light receiving element 70 and the light emitting elements 80 and 80.

The second electrode (negative electrode) 60 is provided with a second central electrode section 61 formed at a position corresponding to the first central electrode section 51 of the first electrode 50, and two second circumferential electrode sections 62 and 62 which are formed around the second central electrode section 61 at positions corresponding to the first circumferential electrode sections 52 and 52 and which uninterruptedly surround the second central electrode section 61 in an arc shape in a plan view.

A let-out electrode section 63*a* is connected to the second central electrode section 61. The let-out electrode section 63*a* is formed to go between the second circumferential electrode sections 62 and 62 on the translucent substrate 41, wrap around the perimeter of one second circumferential electrode section 62, and extend to a side edge side of the translucent substrate 41.

In addition, the abovementioned let-out electrode sections 63*d* and 63*d* are connected to respective ends of the two second circumferential electrode sections 62 and 62. The let-out electrode sections 63*d* and 63*d* are formed to extend to the side edge side of the translucent substrate 41.

In this manner, for the first electrode 50, the let-out electrode sections 63*a* through 63*d*, the light receiving element 70, the light emitting element 80, and the second electrode 60 which are formed on the translucent substrate 41, another translucent substrate 42 is provided on the second electrode 60, and between the two translucent substrates 41 and 42 is sealed by a sealing material 43.

(First Variation of Disposition or the Like)

FIG. 3 is a view that illustrates a variation of disposition for the light emitting elements and light receiving element in FIG. 2, and is a plan view for describing the disposition of a light emitting element, a light receiving element, and the like that make up a reflective photoplethysmogram sensor.

A first variation illustrated in FIG. 3 is a case in which the number of light emitting elements illustrated in FIG. 2 is further increased. In other words, between the light receiving element 70 and the light emitting elements (hereinafter referred to as "second light emitting elements") 80 illustrated in FIG. 2, first light emitting elements 90 are also disposed, and there is a structure in which the light emitting elements 90 and 80 are duplicatively disposed.

Similarly to the second light emitting elements 80 illustrated in FIG. 2, from among the plurality of light emitting elements 90 and 80, first light emitting elements 90 disposed at positions close to the light receiving element 70 are respectively formed above two first circumferential electrode sections 52 and 52 of a first electrode 50 so as to cover the first circumferential electrode sections 52 and 52. The first light emitting elements 90 and 90 respectively form an arc shape in a plan view along the first circumferential electrode sections 52 and 52, and the first light emitting elements 90 and 90 are uninterruptedly formed so as to not be mutually contiguous with each other.

Here, for, among the plurality of light emitting elements 90 and 80, the second light emitting elements 80 disposed at a position far from the light receiving element 70, a minimum distance h between the second light emitting elements 80 and the light receiving element 70 is within a range that satisfies the abovementioned Expression (1). Note that the minimum distance between the light receiving element 70 and the first light emitting elements 90 is assumed not to be within a range that satisfies the abovementioned Expression (1).

In addition, it is desirable that a minimum width in the plan view for a first light emitting element 90 is approximately 5 mm.

Here, the minimum width for a first light emitting element 90 refers to, in a case where the first light emitting element 90 has an arc shape in a plan view, the length of a line orthogonal to respective tangents drawn for the outer peripheral surface and the inner peripheral surface of the arc shape. Note that, in a case a light emitting element has a circular shape in a plan view, the minimum width refers to the diameter of the circle.

Furthermore, the first light emitting elements 90 being disposed at intermediate points of the distance h between the second light emitting elements 80 and the light receiving element 70 is desirable from a viewpoint of facilitating manufacturing. Note that, in FIG. 3, the first light emitting elements 90 are not disposed at the intermediate points due to the nature of the drawing.

In this manner, from among the plurality of the first and second light emitting elements 90 and 80, it is desirable for the first light emitting elements 90 and 90 to each emit light of the same wavelength and the second light emitting elements 80 and 80 to each emit light of the same wavelength, and it is desirable for the first and second light emitting elements 90 and 80 to emit light of mutually different wavelengths.

Furthermore, it is desirable for each of these pluralities of first and second light emitting elements 90 and 80 to be controlled so as to be turned on individually.

In addition, from among the plurality of light emitting elements 90 and 80, it is desirable to subject vital data (biological information), obtained on the basis of light emitted from the second light emitting elements 80 disposed at positions farther away from the light receiving element 70 than the first light emitting elements 90, to data processing by an information processing apparatus 3 described below, the data processing based on vital data obtained on the basis of light emitted from the first light emitting elements 90 disposed at positions close to the light receiving element 70.

Here, the light emitted from the second light emitting elements 80 is irradiated onto an artery deep under skin, and light reflected by the artery is received by the light receiving element 70. Accordingly, because the light penetrates a shallow portion under the skin, vital data obtained by the light receiving element 70 is data that includes noise.

Meanwhile, vital data obtained on the basis of light emitted from the first light emitting elements 90 disposed at positions near the light receiving element 70 is data that includes noise because this light irradiated capillaries at a shallow portion under the skin and does not irradiate an artery. Accordingly, it is possible to calculate valid data from which noise has been subtracted by performing data processing that subtracts this data that includes noise (the vital data obtained on the basis of light emitted from the first light emitting elements 90) from the vital data obtained on the basis of light emitted from the second light emitting elements 80.

In addition, in FIG. 2, the let-out electrode sections 63*a*, 63*b*, 63*c*, and 63*d* are disposed as let-out from only one side edge of the translucent substrate 41, but in the first variation illustrated in FIG. 3, the let-out electrode sections 63*a*, 63*b*, 63*c*, and 63*d* are disposed let-out on two side edges of the translucent substrate 41 that oppose each other.

(Second Variation of Disposition or the Like)

Figure 4:
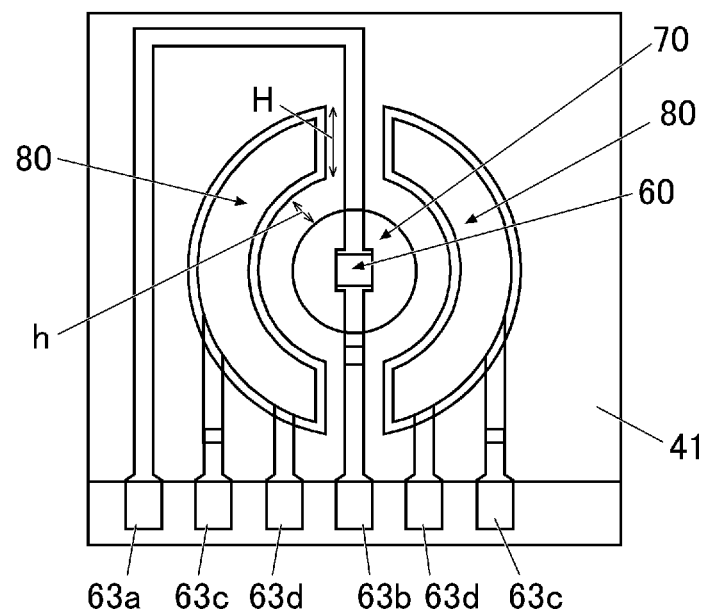
FIG. 4 is a view that illustrates a variation of the disposition or the like in FIG. 2.

FIG. 4 is a variation of FIG. 2, and is a plan view for describing the disposition of a light emitting element, a light receiving element, and the like that make up a reflective photoplethysmogram sensor.

A second variation illustrated in FIG. 4 is a case in which the minimum width (reference symbol H in FIG. 4) in the plan view for the light emitting elements 80 illustrated in FIG. 2 is made to be thicker, and because the remaining configuration is similar, similar reference symbols are applied to similar components, and description thereof is omitted.

(Third Variation of Disposition or the Like)

Figure 5:
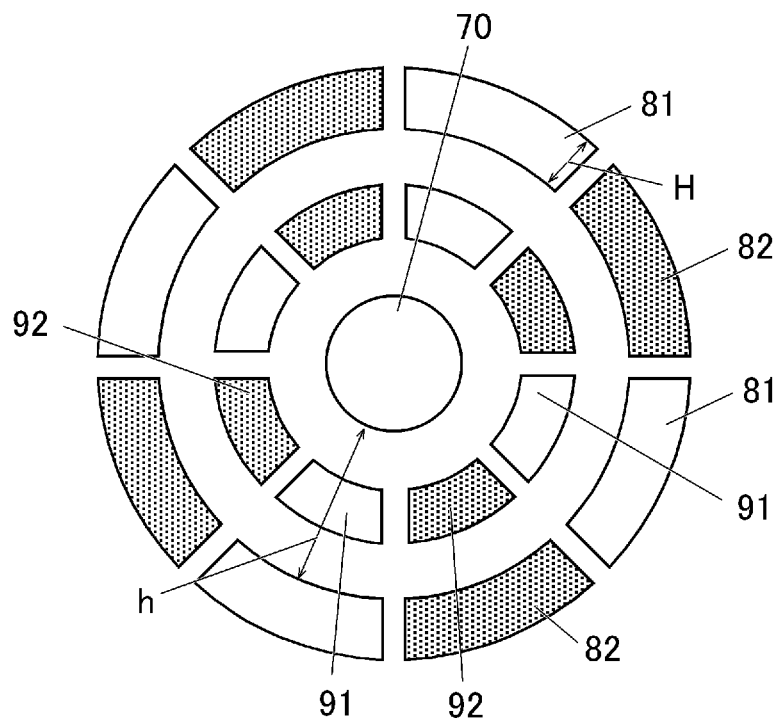
FIG. 5 is a view that illustrates a variation of the disposition or the like in FIG. 2.

FIG. 5 is a variation of FIG. 2, and is a plan view for describing the disposition of a light emitting element, a light receiving element, and the like that make up a reflective photoplethysmogram sensor.

In a third variation illustrated in FIG. 5, two types of second light emitting elements 81 and 82 having different emission wavelengths are used, and a plurality of these two types of second light emitting elements 81 and 82 are alternatingly disposed on concentric circles centered on the light receiving element 70. Each of the second light emitting elements 81 and 82 forms an arc shape in a plan view.

In addition, a plurality of first light emitting elements 91 and 92 are also disposed between the plurality of second light emitting elements 81 and 82 and the light receiving element 70. The plurality of first light emitting elements 91 and 92 respectively emit two types of light having different emission wavelengths, similarly to the second light emitting elements 81 and 82. Each of the first light emitting elements 91 and 92 also forms an arc shape in a plan view.

Furthermore, it is desirable for the plurality of first and second light emitting elements 91, 92, 81, and 82 to be controlled so as to emit light (be turned on) individually.

Here, for, among the plurality of first and second light emitting elements 91, 92, 81, and 82, the second light emitting elements 81 and 82 disposed at a position far from the light receiving element 70, a minimum distance h between the second light emitting elements 81 and 82 and the light receiving element 70 is within a range that satisfies the abovementioned Expression (1). Note that the minimum distance between the light receiving element 70 and the first light emitting elements 91 and 92 is assumed not to be within a range that satisfies the abovementioned Expression (1).

In addition, from among the plurality of light emitting elements 91, 92, 81, and 82, it is desirable to subject vital data (biological information), obtained on the basis of light emitted from the second light emitting elements 81 and 82 disposed at positions farther away from the light receiving element 70 than the first light emitting elements 91 and 92, to data processing by the information processing apparatus 3, the data processing based on vital data (biological information) obtained on the basis of light emitted from the first light emitting elements 91 and 92 disposed at positions close to the light receiving element 70.

(Fourth Variation of Disposition or the Like)

FIG. 6 is a variation of FIG. 2, and is a plan view for describing the disposition of a light emitting element, a light receiving element, and the like that make up a reflective photoplethysmogram sensor.

In a fourth variation illustrated in FIG. 6, two types of second light emitting elements 81 and 82 having different emission wavelengths are used, and these two types of second light emitting elements 81 and 82 are alternatingly disposed on concentric circles centered on the light receiving element 70. The second light emitting elements 81 and 82 each forms a circular shape in a plan view, differing from the arc shape in a plan view illustrated in FIG. 5.

In addition, for the second light emitting elements 81 and 82, the respective minimum distance h between the second light emitting elements 81 and 82 and the light receiving element 70 is within a range that satisfies Expression (1) described above.

It is also desirable for the plurality of second light emitting elements 81 and 82 to be controlled so as to emit light (be turned on) individually.

Note that, although only the light emitting elements 81, 82, 91, and 92 and the light receiving element 70 are illustrated in FIGS. 5 and 6, similarly to FIG. 2, two translucent substrates 41 and 42, a first electrode 50, let-out electrode sections 93a, 93b, 93c, and 93d, a second electrode 60, a sealing material 43, and the like are provided.

Second Embodiment

A second embodiment is, as described above, a case in which a plurality of light receiving elements are disposed on concentric circles centered on a light emitting element, and the remaining configuration is similar to that of the first embodiment.

FIGS. 7A through 7D are schematic views for describing the disposition of a light emitting element, a light receiving element, and the like that make up a reflective photoplethysmogram sensor. FIG. 7A is a plan view, FIG. 7B is a plan view that decomposes each member, FIG. 7C is a cross-sectional view taken along arrows C-C', and FIG. 7D is a cross-sectional view taken along arrows D-D'.

As illustrated in FIGS. 7A through 7D, for a detector 14, a plurality of let-out electrode sections 63a, 63b, 63c, and 63d for an optically transparent first electrode (positive electrode) 50 and an optically transparent second electrode (negative electrode) 60 are formed on a translucent substrate 41.

The first electrode 50 is provide with a first central electrode section 51 formed at the center of the translucent substrate 41, and first circumferential electrode sections 52 and 52 disposed on concentric circles centered on the first central electrode section 51.

The first circumferential electrode sections 52 and 52 each form an arc shape in a plan view, and are uninterruptedly formed so that the first circumferential electrode sections 52 and 52 are not mutually contiguous with each other.

In addition, the first central electrode section 51 is formed extending on the let-out electrode section 63b side. Furthermore, the two first circumferential electrode sections 52 and 52 are also formed extending on the let-out electrode section 63c side.

The let-out electrode sections 63a, 63b, 63c, and 63d are formed on the translucent substrate 41, and are made to be wiring that is let out to a side edge of the translucent substrate 41.

The light emitting element 80 is formed above the first central electrode section 51 in the first electrode 50, so as to cover the first central electrode section 51. The light emitting element 80 forms a circular shape in a plan view.

In addition, light receiving elements 70 and 70 are respectively formed, over the two first circumferential electrode sections 52 and 52 in the first electrode 50, so as to cover the first circumferential electrode sections 52 and 52. The light receiving elements 70 and 70 respectively form an arc shape in a plan view along the first circumferential electrode sections 52 and 52, and the light receiving elements 70 and 70 are uninterruptedly formed so as to not be mutually contiguous with each other.

In this manner, the two light receiving elements 70 and 70 formed on the first circumferential electrode sections 52 and 52 are disposed on concentric circles centered on the center point of the light emitting element 80.

In addition, in FIG. 7, although a minimum width W for a light receiving element 70 in the plan view is greater than a minimum distance h between the light receiving element 70 and the light emitting element 80, from a viewpoint of improving measurement accuracy, it is desirable for the minimum width for a light receiving element 70 to be equal to the minimum distance h between the light receiving element 70 and the light emitting element 80.

Here, similarly to the minimum width H for the light emitting element 80 illustrated in FIG. 2, the minimum width W in the plan view for a light receiving element 70 refers to, in a case where the light receiving element 70 has an arc shape in a plan view, the length of a line orthogonal to respective tangents drawn for the outer peripheral surface and the inner peripheral surface of the arc shape. Note that, in a case a light receiving element has a circular shape in a plan view, the minimum width refers to the diameter of the circle.

A second electrode 60 is also formed on the light receiving elements 70 and 70 and the light emitting element 80.

The second electrode (negative electrode) 60 is provided with a second central electrode section 61 formed at a position corresponding to the first central electrode section 51 of the first electrode 50, and two second circumferential electrode sections 62 and 62 which are formed around the second central electrode section 61 at positions corresponding to the first circumferential electrode sections 52 and 52 and which uninterruptedly surround the second central electrode section 61 in an arc shape in a plan view.

A let-out electrode section 63a is connected to the second central electrode section 61. The let-out electrode section 63a is formed to go between the second circumferential electrode sections 62 and 62 on the translucent substrate 41, wrap around the perimeter of one second circumferential electrode section 62, and extend to a side edge side of the translucent substrate 41.

In addition, the abovementioned let-out electrode sections 63d and 63d are connected to respective ends of the two second circumferential electrode sections 62 and 62. The let-out electrode sections 63d and 63d are formed to extend to the side edge side of the translucent substrate 41.

In this manner, for the first electrode 50, the let-out electrode sections 63a through 63d, the light receiving element 70, the light emitting element 80, and the second electrode 60 which are formed on the translucent substrate 41, another translucent substrate 42 is provided on the second electrode 60, and between the two translucent substrates 41 and 42 is sealed by a sealing material 43.

(Fifth Variation of Disposition or the Like)

Figure 8:
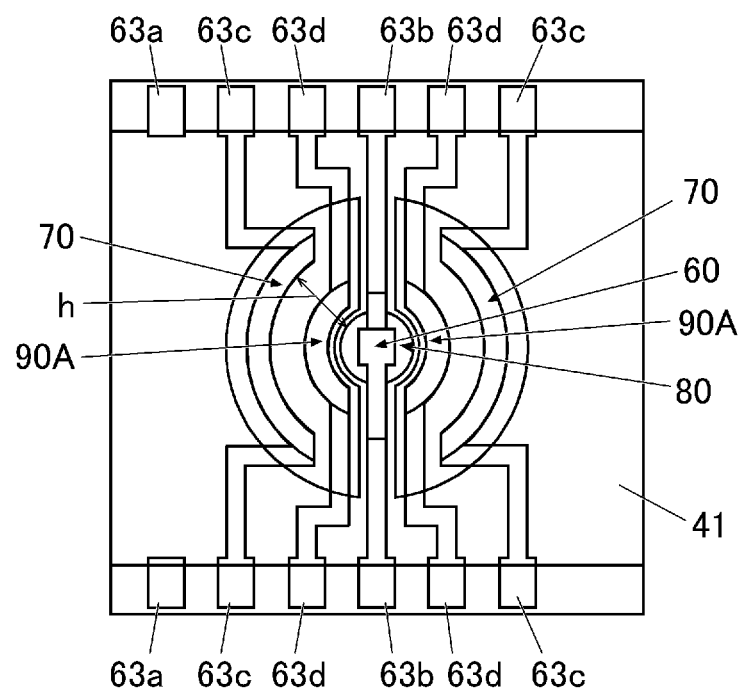
FIG. 8 is a view that illustrates a variation of the disposition or the like in FIG. 7.

FIG. 8 is a variation of FIG. 7, and is a plan view for describing the disposition of a light emitting element, a light receiving element, and the like that make up a reflective photoplethysmogram sensor.

A fifth variation illustrated in FIG. 8 is a case in which the number of light receiving elements illustrated in FIG. 7 is further increased. In other words, between the light emitting element 80 and the light receiving elements (hereinafter referred to as "second light receiving elements") 70 illustrated in FIG. 7, first light receiving elements 90A are also disposed, and there is a structure in which the light receiving elements 70 and 90A are duplicatively disposed. Note that, FIG. 8 is a case in which the light receiving element and light emitting elements illustrated in FIG. 3 have swapped dispositions, and the remaining configuration is similar to that in FIG. 3 and thus description thereof is omitted.

In addition, from among the plurality of light receiving elements 70 and 90A, it is desirable to subject vital data (biological information), obtained on the basis of light emitted from the second light receiving elements 70 disposed at positions farther away from the light emitting element 80 than the first light receiving elements 90A, to data processing by the information processing apparatus 3 described below, the data processing based on vital data (biological information) obtained on the basis of light emitted from the first light receiving elements 90A disposed at positions close to the light emitting element 80.

In addition, in the second embodiment, it is also possible to apply swapped dispositions for light receiving elements and light emitting elements (in other words, configurations in which light receiving elements are disposed on concentric circles centered on a light emitting element) in the second variation through the fourth variation described above.

Note that, in the reflective photoplethysmogram sensor according to the present invention, configuration may be taken so that there is a plurality of different minimum distances between a light emitting element and a light receiving element, and the light emitting element and light receiving element having a minimum distance suitable for sensing are selected.

In other words, it is desirable to use a device in which there is a plurality of one or both of a light emitting elements and a light receiving elements and there is a plurality of different minimum distances between a light emitting element and a light receiving element, in order to provide a mechanism for extracting the minimum distance which is most suitable for sensing.

Figure 9A:
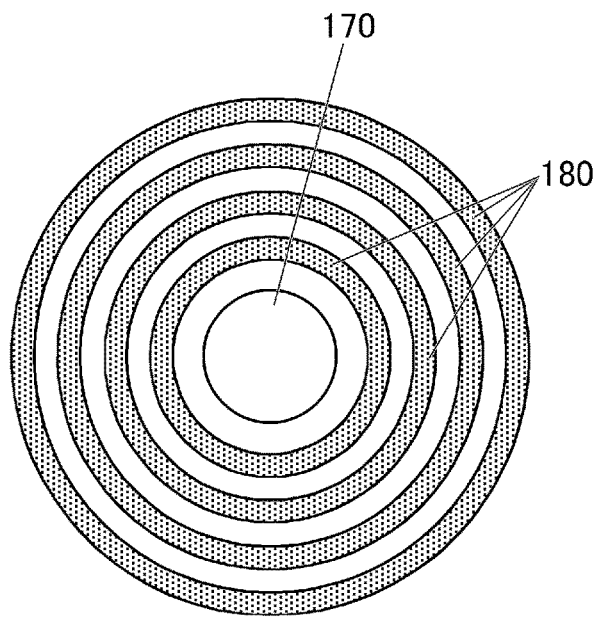
FIG. 9A through 9C are schematic views for describing other examples of a reflective photoplethysmogram sensor.
Figure 9B:
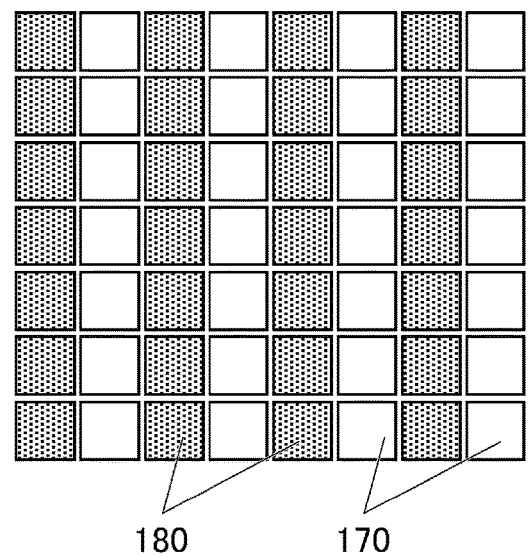

For example, a device in which a plurality of light emitting elements 180 are disposed on concentric circles centered on one light receiving element 170 as illustrated in FIG. 9A and there is a plurality of different minimum distances, or a device in which a plurality of light receiving elements 170 and a plurality of light emitting elements 180 are disposed in a matrix-shape as illustrated in FIG. 9B may be given. Configuration is such that each pixel can be individually driven.

Figure 9C:
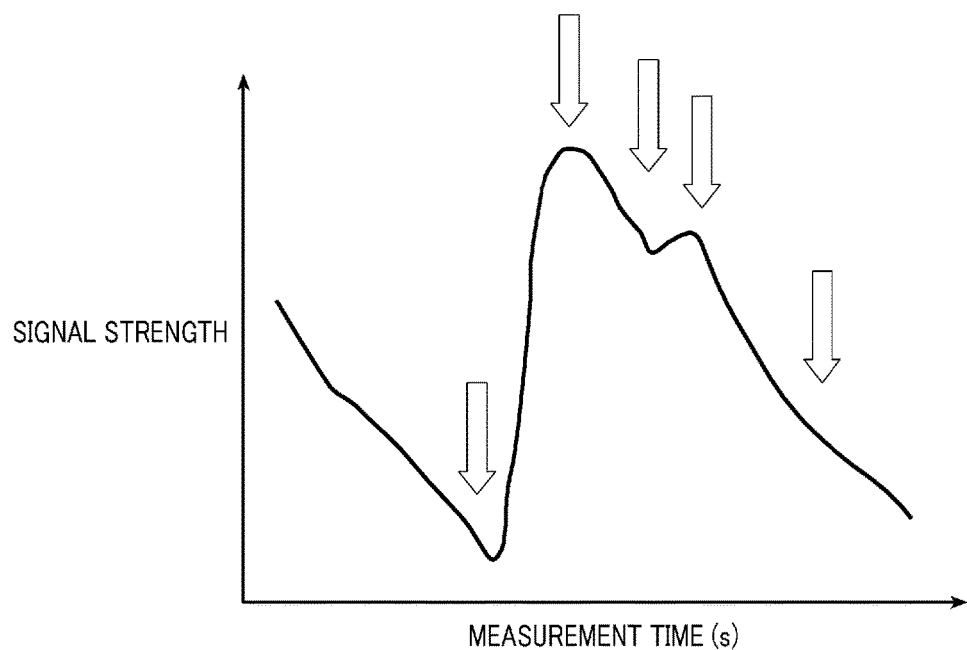

Distinguishing which minimum distance is most suitable for sensing is performed in accordance with whether or not it is possible to clearly confirm inflection points in a waveform of vital data obtained from a light receiving element, as illustrated in FIG. 9C (arrows in FIG. 9C indicate inflection points). For example, because the inflection points are hidden when there is a lot of noise, it is necessary to increase the amplitude (height) in order to obtain a more accurate waveform, and it is effective to capture a location where there is a large change in volume, in accordance with PPG principles.

1.2 [Example of Overall Configuration of Reflective Photoplethysmogram Sensor]

The overall configuration of a reflective photoplethysmogram sensor can take various forms and aspects.

For example, as the basic overall configuration, it is desirable to have a configuration provided with a light emitting element that, on the basis of a signal from an oscillator, is driven to flicker and emit light in accordance with a frequency higher than a frequency of a plethysmogram of a living body; a light receiving element that receives light which is light emitted from the light emitting element and outside light which are reflected by biological tissue to be measured, and generates a signal having a signal level corresponding to the amount of received light; an extraction means that extracts a signal component in accordance with the outside light from the signal generated by the light receiving element; a reduction means that, by subtracting the signal component extracted by the extraction means from the signal generated by the light receiving element, reduces a noise signal due to outside light or the like in the signal generated by the light receiving element; and a means for, on the basis of the signal in which the noise signal component due to the outside light or the like has been reduced by the reduction means, generating a signal representing a plethysmogram of the living body to be measured.

1.3 [Components of Reflective Photoplethysmogram Sensor]

From among the various components of a reflective photoplethysmogram sensor, description is given in detail regarding a light emitting element and a light receiving element, which are the main components.

<Light Emitting Element>

In the present invention, a light emitting element is used as a light source for light for irradiating biological tissue.

As the light emitting element, it is possible to use an organic light emitting diode (OLED) or an inorganic light emitting diode (LED), and, in particular, although no limitation is made, using, as a light emitting element according to the present invention, an organic electroluminescent diode (also referred to as an "OLED", an "organic EL diode", or an "organic photodiode") which is a light emitting element configured by a planar organic layer is desirable from viewpoints of having good wearability due to being flexible, and being able to reduce wavelength variation or luminance variation.

In particular, it is desirable to have a configuration in which a wavelength conversion filter for converting visible light from an organic EL diode, which emits red light, into near-infrared light (IR) is disposed on the organic EL diode.

In addition, an LED and a light guide plate may be used as a planar light emitting element. In a display backlight, a method is employed in which an LED is disposed at the edge of the light guide plate, and light is incident from the side edge of the light guide plate.

Furthermore, micro-LEDs with a resolution at which the micro-LEDs can be treated as a surface may be used. It is more desirable to provide a scattering layer in order to mitigate the luminance directly above an LED from locally increasing.

(Organic EL Element)

As an organic EL diode suitable for the present invention, for example, it is possible to give a configuration that has a positive electrode and a negative electrode on a flexible resin substrate, in which an organic functional group that includes a light emitting layer is sandwiched between the positive electrode and the negative electrode which are at opposing positions. Furthermore, in accordance with an objective, there may be a configuration that is appropriately combined with a sealing member or various functional layers such as a gas barrier layer or a light extraction layer.

Examples of representative configurations for an organic EL diode according to the present invention are listed below, but the configuration of an organic EL diode that can be applied to the present invention is not limited to the exemplified configurations.

(1) Positive electrode/light emitting layer/negative electrode
(2) Positive electrode/light emitting layer/electron transport layer/negative electrode
(3) Positive electrode/hole transport layer/light emitting layer/negative electrode
(4) Positive electrode/hole transport layer/light emitting layer/electron transport layer/negative electrode
(5) Positive electrode/hole transport layer/light emitting layer/electron transport layer/electron injection layer/negative electrode
(6) Positive electrode/hole injection layer/hole transport layer/light emitting layer/electron transport layer/negative electrode
(7) Positive electrode/hole injection layer/hole transport layer/(electron blocking layer/) light emitting layer/(hole blocking layer/) electron transport layer/electron injection layer/negative electrode For the organic EL diode, an electric field is applied from outside, holes are injected from the positive electrode to a hole transport layer, and electrons are injected from the negative electrode to an electron transport layer. Injected carriers move by hopping between molecules. The holes and electrons recombine in the light emitting layer, and generate excitons which are electrically neutral. The excitons radiatively deactivate by emitting light in accordance with light emission quantum efficiency. Light generated in an organic layer is taken out into the air from a light extraction surface.

Details of each specific constituent layer that makes up an organic EL diode that can be applied to the present invention and methods of manufacturing the same are not particularly limited, and it is possible to employ publicly-known constituent materials or manufacturing methods. For example, it is possible to refer to details described in Japanese Patent Application Publication No. 2013-089608, Japanese Patent Application Publication No. 2014-120334, Japanese Patent Application Publication No. 2015-201508, International Publication No. 2018/51617, and the like.

(Wavelength Conversion Filter)

It is desirable for an organic EL diode according to the present invention to be provided with a wavelength conversion filter for converting visible light from the organic EL diode into near-infrared light.

It is desirable for the wavelength conversion filter according to the present invention to include a luminous body (for example, a light emitting colorant or the like) which has a wavelength conversion ability. If the wavelength conversion filter according to the present invention includes a light emitting colorant having a wavelength conversion ability, for example, in particular the form or the method of manufacturing the wavelength conversion filter is not limited and is determined, as appropriate, in accordance with an objective or an intended use.

It is desirable for the wavelength conversion filter according to the present invention to have a function of absorbing light from an organic EL diode that emits light within a range for a visible light region (380-780 nm) including a near-red-light region, desirably within a range for a green-through-red region (495-750 nm) including the near-red-light region, and particularly desirably within a range for a red region (600-700 nm); emitting near-infrared light, for example in a region that is greater than 700 nm and less than or equal to 1500 nm; and furthermore performing a conversion to near-infrared light having a light-emission maxima near 850 nm.

Even with a method of production in which the wavelength conversion filter and the organic EL diode are each separately manufactured and then pasted together, the wavelength conversion filter may be directly coated and laminated on the organic EL diode. A cut filter for excluding radiated light without performing a wavelength conversion may be laminated or included, as necessary.

From a perspective of miniaturization and maintaining flexibility, the thickness of a wavelength conversion filter according to the present invention is desirably in a range of 0.01-1000 μm, more desirably in a range of 1-500 μm, and even more desirably in a range of 10-300 μm.

In addition to a light emitting colorant, a wavelength conversion filter according to the present invention, as necessary, may include various types of well-known additives, such as a colorant or a light stabilizer, an antioxidant, a surfactant, a flame retardant, an inorganic additive, a transparentizing agent, an ultraviolet light absorbent, a filler, or light scattering particles.

<Light Receiving Element>

A light receiving element according to the present invention functions as a sensor that detects, from among light irradiated from a light emitting element onto biological tissue, light reflected by the biological tissue, and converts the detected light into electricity.

As a light receiving element, it is desirable to use a planar organic photodiode (OPD) or organic photovoltaics (OPV), and in particular using an OPD is desirable from viewpoints of having good wearability due to being flexible, and being able to reduce wavelength variation or luminance variation.

(1) Organic Photodiode

It is possible to use a conventionally known organic photodiode (OPD) as a light receiving element according to the present invention.

For example, an organic photodiode has as basic components a positive electrode that includes a transparent electrically conductive film such as indium-tin oxide (ITO) formed in accordance with a sputtering method, a resistance heating vapor deposition method, or the like on an optically transparent substrate made of resin, glass, or the like, an photoelectric conversion layer with a configuration formed by respectively depositing an electron-donating layer and an electron-accepting layer in accordance with the resistance heating vapor deposition method or the like on the positive electrode, and furthermore a negative electrode that includes a metal formed in accordance with the same resistance heating vapor deposition method or the like on top of the photoelectric conversion layer.

When an organic photodiode having such a configuration is irradiated with light, light absorption in the photoelectric conversion region occurs, and excitons are formed. Next, the carriers are separated with electrons moving through the electron-accepting layer to the negative electrode, and holes moving through the electron-donating layer to the positive electrode. As a result, electromotive force occurs between both electrodes, and it is possible to extract an electrical signal by connecting an external circuit.

The photoelectric conversion layer can include a single layer or a plurality of layers. It is possible to have various combinations for the photoelectric conversion layer, for example: intrinsic layer (I layer), p-type layer/I layer, I layer/n-type layer, p-type layer/I layer/n-type layer, or p-type layer/n-type layer.

For example, it is possible to use something having the structure illustrated in FIG. 13D of US Patent Application Publication No. 2017/0156651. In addition, in relation to various types of organic materials used in an organic photodiode, reference is made to Japanese Translation of PCT International Application Publication No. 2017-532546 and Japanese Patent Application Publication No. 2006-261172.

(2) Organic Photovoltaics

As a light receiving element according to the present invention, it is possible to use various forms of conventionally known organic photovoltaics (OPV).

For example, it is possible to use a bulk heterojunction type organic photoelectric conversion element having a basic configuration in which, on one surface of a substrate, a positive electrode which is a transparent electrode, a hole transport layer, a photoelectric conversion layer which is a bulk heterojunction layer, an electron transport layer, and a negative electrode are sequentially laminated.

Note that there may be other layers such as a hole blocking layer, an electron blocking layer, an electron injection layer, a hole injection layer, or a smoothing layer.

Note that the photoelectric conversion layer is a layer that converts light energy into electrical energy, and is configured by having a bulk heterojunction layer that uniformly mixes p-type semiconductor material and n-type semiconductor material.

The p-type semiconductor material relatively functions as an electron donor, and the n-type semiconductor material relatively functions as an electron acceptor.

Here, the electron donor and electron acceptor are an "electron donor and electron acceptor for which electrons move from the electron donor to the electron acceptor when light is absorbed, and which form pairs of holes and electrons (a charge separation state)", do not simply donate or accept electrons as with an electrode, and donate or accept electrons in accordance with a photoreaction.

In addition, for the purpose of further improving solar utilization (photoelectric conversion efficiency), there may be a tandem type configuration (a configuration that has a plurality of bulk heterojunction layers) in which such a photoelectric conversion element is laminated.

As the p-type semiconductor material, various condensed polycyclic aromatic compounds or conjugated compounds may be given.

As an example of the n-type semiconductor material, a polymer compound that includes as a skeleton a fullerene, octaaza porphyrin, a perfluoro compound of the p-type semiconductor, or an aromatic carboxylic acid anhydride or an imidized compound thereof, such as naphthalenetetracarboxylic dianhydride, naphthalenetetracarboxylic diimide, perylenetetracarboxylic dianhydride, or perylenetetracarboxylic diimide may be given.

2. [Biological Information Measurement Apparatus]

A reflective photoplethysmogram sensor according to the present invention can be applied to a biological information measurement apparatus having various forms in accordance with an objective.

Description is given below regarding examples of application.

First Application Example

Figure 10:
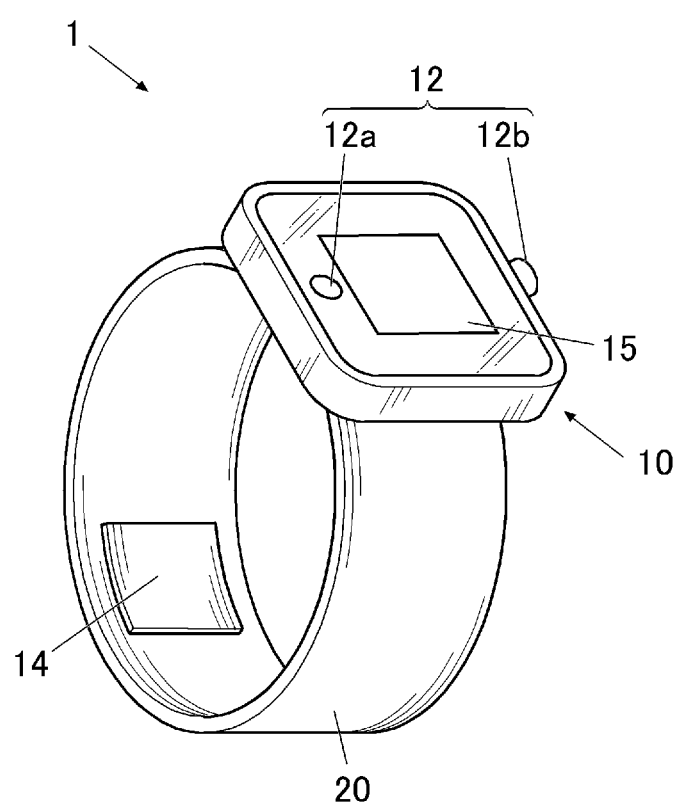
FIG. 10 is a view for describing an example of an exterior configuration of a biological information measurement apparatus.

FIG. 10 is a perspective view of a biological information measurement apparatus which uses a reflective photoplethysmogram sensor and which can be wound around a wrist.

A biological information measurement apparatus 1 has a main body 10 which is worn on a wrist of a patient as with a wristwatch. Specifically, the main body 10 is provided with a belt 20, and can be worn on the wrist of the patient in accordance with the belt 20. In addition, a detector 14 which is provided with a light emitting element 80, a light receiving element 70, and the like described below is disposed on the inside of the belt 20, and the detector 14 and the main body 10 are electrically connected.

Light of a certain amount is constantly outputted from the light emitting element 80 and irradiated within the living body, and an amount of light that is reflected changes due to the amount of oxygen-bonded hemoglobin flowing in blood. The light receiving element 70 can output to the main body a signal that depends on an amount of received light for the reflected light, and measure an oxygen concentration in the patient's blood.

The main body 10 is formed in a flat shape, and an operating unit 12 and a display 15 are provided on the circumference or surface thereof. In addition, an electric circuit or the like which fulfills functions correspond to a controller 11, a recorder 13, or the like (refer to FIG. 11) is accommodated within the main body 10.

For example, the operating unit 12 is configured by being provided with a power switch 12a, a timing switch (operation switch) 12b, and the like.

Second Application Example

Figure 11:
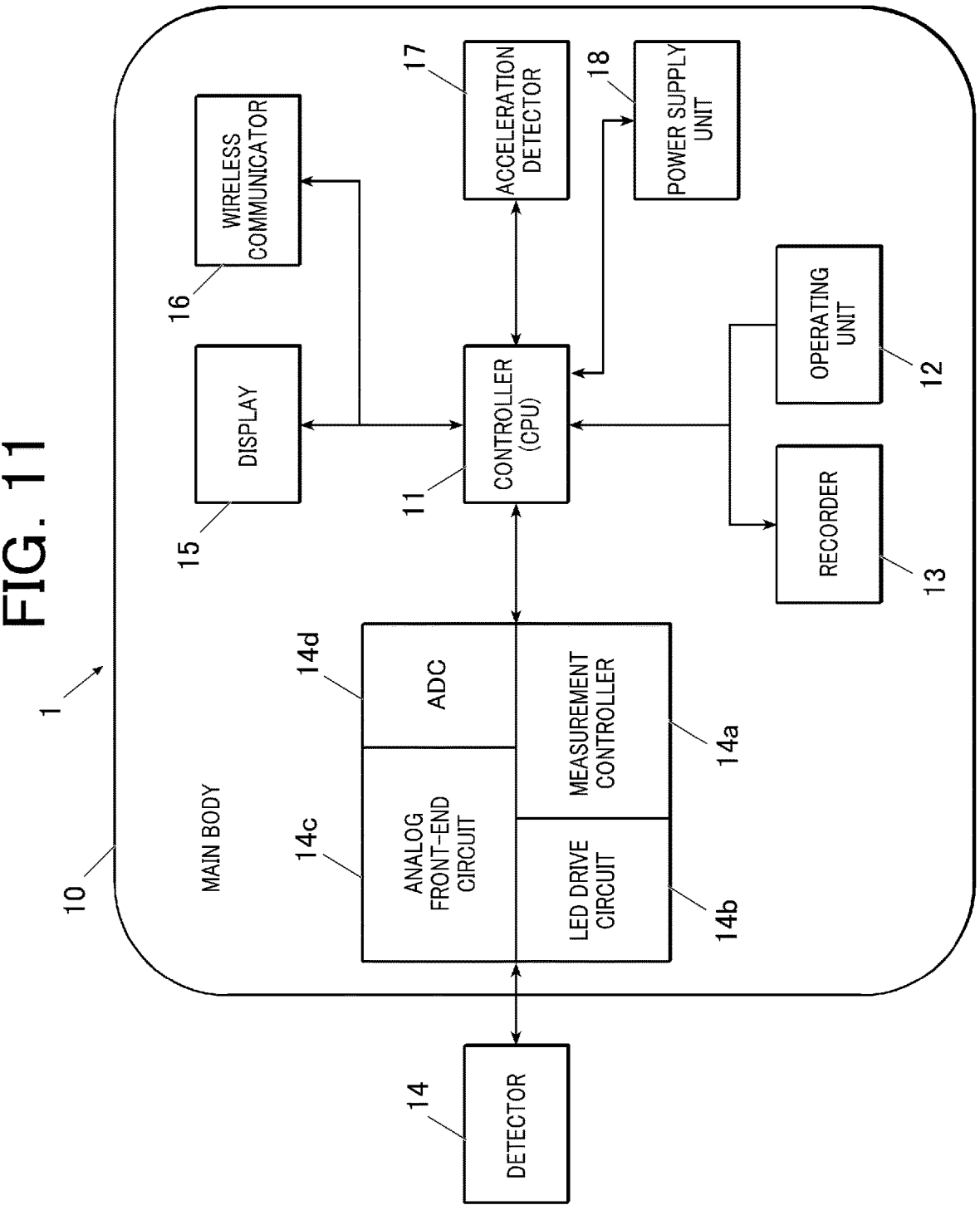
FIG. 11 is a view for describing an example of a functional configuration of the biological information measurement apparatus.

FIG. 11 is a view for describing an example of a functional configuration of the biological information measurement apparatus 1. As illustrated in FIG. 11, the biological information measurement apparatus 1 is configured by being provided with the controller 11, the operating unit 12, the recorder 13, the detector 14, the display 15, a wireless communicator 16, an acceleration detector 17, a power supply unit 18, and the like.

The controller 11 is configured in accordance with a central processing unit (CPU), a random-access memory (RAM), and the like. The CPU of the controller 11 reads out various programs such as a system program or a processing program that are recorded in the recorder 13, deploys the read-out program to the RAM, and executes various processing in accordance with the deployed program.

In addition, the controller 11 has a clock function unit, and can obtain the date and time which are the measurement date/time of vital data from this clock function unit.

The operating unit 12 is a detector that detects an instruction from an operator and is provided with various switches, various function buttons, or the like, and outputs an operation signal from these to the controller 11.

The recorder 13 is configured from, for example, a semiconductor non-volatile memory. The recorder 13 records a system program, various programs, parameters or files necessary for these programs to be executed, or the like, which are necessary for causing the biological information measurement apparatus 1 according to the present embodiment to function.

For example, the recorder 13 continuously records vital data that is being measured in a duration from the start of measurement until measurement ends. Note that vital data may be recorded each certain amount of time in the duration from the start of measurement until the end of measurement.

The detector 14 is a data obtainment unit that obtains vital data of a patient by applying the reflective photoplethysmogram sensor according to the present invention, and, as described above, is provided with a light emitting element, a light receiving element, and the like, and is configured so as to be able to be worn on a living body site such as a wrist.

The detector 14 controls a light emitting element drive circuit 14b in accordance with a measurement controller 14a, emits red light and infrared light in accordance with the light emitting element provided in the detector 14 toward the living body site, in accordance with an analog front-end circuit 14c performs noise removal or signal amplification on an analog signal for reflected light which is from the living body site and is received by the light receiving element provided in the detector 14 and prepares the analog signal as a voltage signal for inputting to an AD converter 14d, and converts the voltage signal to digital data in accordance with the AD converter 14d.

After making the conversion to digital data in accordance with the AD converter 14d, vital data such as $SpO_2$ or a pulse rate is calculated by the controller 11 on the basis of this digital data. The calculated vital data is recorded in the recorder 13.

The display 15 is configured by being provided with a liquid crystal display (LCD) or the like, for example, displays in accordance with a dot matrix method for example, and displays in accordance with an instruction for a display signal inputted from the controller 11.

The wireless communicator 16 has a wireless interface for transmitting and receiving data to and from the information processing apparatus 3 in accordance with wireless communication such as Bluetooth (registered trademark) or Wi-Fi (registered trademark), for example.

The acceleration detector 17 detects movement of the patient on the basis of change in acceleration. Specifically, the acceleration detector 17 generates an acceleration signal in accordance with acceleration applied thereon in accordance with, for example, body motion of the patient, and outputs the acceleration signal to the controller 11.

The power supply unit 18 supplies each unit of the biological information measurement apparatus 1 with power needed for these units to operate. The power supply unit 18 supplies power outputted from a battery (not illustrated) at an operating voltage for each unit.

(Configuration of Biological Information Processing Apparatus)

The information processing apparatus 3 is an apparatus that can analyze vital data transmitted from the biological information measurement apparatus 1. As the information processing apparatus 3, for example it is possible to employ a smartphone, a tablet, a personal computer (PC), or the like, but there is no particular limitation.

Figure 12:
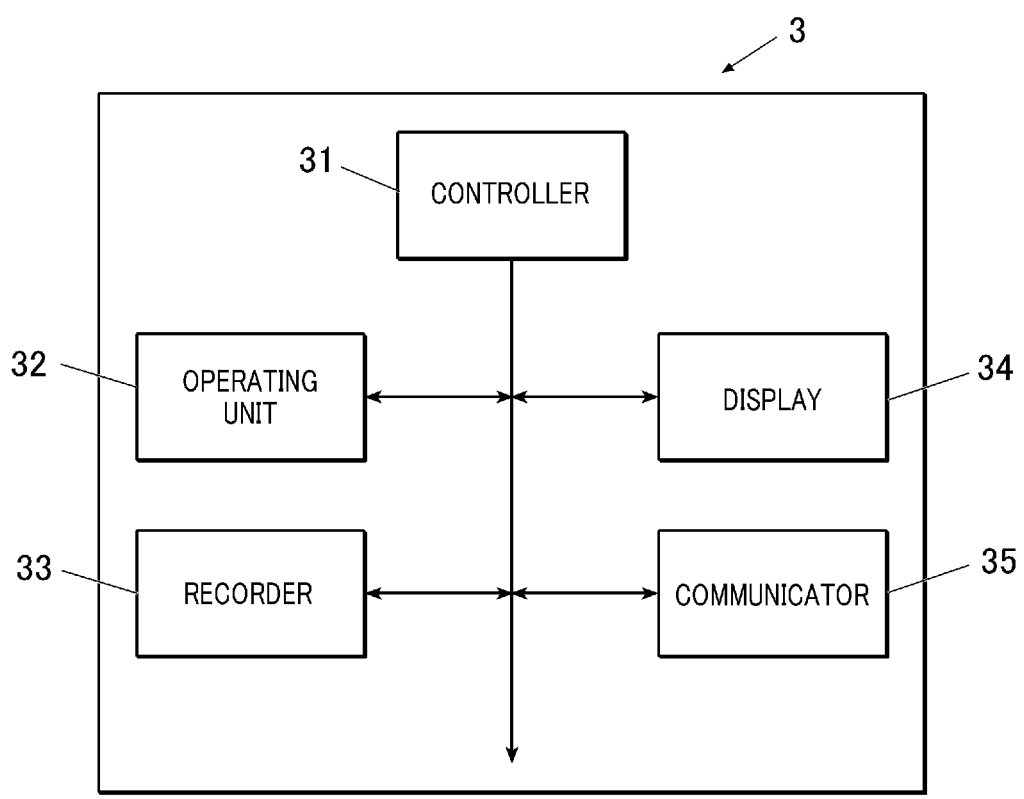
FIG. 12 is a view for describing an example of a functional configuration of an information processing apparatus.

FIG. 12 illustrates an example of a functional configuration of the information processing apparatus 3. As illustrated in FIG. 12, the information processing apparatus 3 is, for example, configured by being provided with a controller 31, and operating unit 32, a recorder 33, a display 34, a communicator 35, or the like.

The controller 31 is configured by a CPU, a RAM, and the like. The CPU of the controller 31 reads out various programs such as a system program or a processing program that are recorded in the recorder 33, deploys the read-out program to the RAM, and executes various processing in accordance with the deployed program.

Specifically, in a case where first and second light emitting elements 90 and 80 (91, 92, 81, and 82) are respectively disposed at positions having different distances from the light receiving element 70 on concentric circles centered on the light receiving element 70 (for example, the case of the disposition in FIG. 3 or FIG. 5) in the biological information measurement apparatus 1, the controller 31 performs processing for, from among the vital data outputted from the biological information measurement apparatus 1, calculating valid vital data from which noise has been removed, by subtracting vital data obtained on the basis of the light emitted from the first light emitting elements 90 (91 and 92) from the vital data obtained on the basis of the light emitted from the second light emitting elements 80 (81 and 82).

In addition, in the case where first and second light receiving elements 70 and 90A are respectively disposed at positions having different distance from the light emitting element 80 on concentric circles centered on the light emitting element 80 (for example, the case of the disposition in FIG. 8), the controller 31 performs processing for, from among the vital data outputted from the biological information measurement apparatus 1, calculating valid vital data from which noise has been removed, by subtracting vital data obtained on the basis of the light received by the first light receiving elements 90A from vital data obtained on the basis of light received by the second light receiving elements 70.

The operating unit 32 is provided with various switches, various function buttons, a touch panel, or the like, and outputs operation signals therefrom to the controller 31.

The recorder 33 is configured from, for example, a semiconductor non-volatile memory. The recorder 33 records a system program, various programs, parameters or files necessary for these programs to be executed, or the like.

For example, vital data outputted from the biological information measurement apparatus 1 is recorded in the recorder 33.

Specifically, in a case where first and second light emitting elements 90 and 80 (91, 92, 81, and 82) are respectively disposed at positions having different distances from the light receiving element 70 on concentric circles centered on the light receiving element 70 (for example, the case of the disposition in FIG. 3 or FIG. 5) in the biological information measurement apparatus 1, vital data based on the first light emitting elements 90 (91, 92), vital data based on the second light emitting elements 80 (81, 82), or valid vital data resulting from subtracting vital data obtained on the basis of the light emitted from the first light emitting elements 90 (91 and 92) from the vital data obtained on the basis of the light emitted from the second light emitting elements 80 (81 and 82) is recorded.

Furthermore, in a case where first and second light receiving elements 70 and 90A are respectively disposed at positions having different distance from the light emitting element 80 on concentric circles centered on the light emitting element 80 (for example, the case of the disposition in FIG. 8), vital data obtained on the basis of light received by the first light receiving element 90A, vital data obtained on the basis of light received by the second light receiving element 70, or valid vital data obtained by subtracting vital data obtained on the basis of the light received by the first light receiving elements 90A from vital data obtained on the basis of light received by the second light receiving elements 70 is recorded.

The display 34 is configured by being provided with a monitor such as a cathode-ray tube (CRT) or a liquid crystal display (LCD), for example, and displays various screens in accordance with an instruction for a display signal inputted from the controller 31.

The communicator 35 has an interface for transmitting and receiving data to and from the biological information measurement apparatus 1 in accordance with wireless communication such as Bluetooth or Wi-Fi, for example. The communicator 35 may have a wired interface such as USB.

EXAMPLE

Description is given below in detail for the present invention by giving examples, but the present invention is not limited to these examples.

Reflective photoplethysmogram sensors 1-11 in which the minimum distance h (mm) between the light emitting element and light receiving element is respectively changed were designed, each sensor was worn on a back of an arm side, a wrist ulna side, a wrist radius side, on the abdomen, or on the chest, and an AC/DC value described below was measured.

Specifically, "KPD30S" (made by Kyoto Semiconductor Co., Ltd.) was used as a light receiving element. As the light emitting element, a ring-shaped light source was obtained by masking, so that light not from a ring section is cut, a device that achieves a peak wavelength of 790 nm by pasting a wavelength conversion film onto a 60×80 mm OLED panel (peak wavelength 630 nm), and this ring-shaped light source was used.

The light receiving element was disposed and fixed at the center of this ring-shaped light source, the ring diameter was adjusted so that the minimum distance h between the light receiving element and the ring-shaped light source became as indicated in the following Table I and Table II, and the reflective photoplethysmogram sensors 1-11 with the structure as illustrated in FIG. 2 were achieved. The width of the ring-shaped light source was set to 2 mm, the amount of light was adjusted between 25-100 mA/m$^2$, and desirable conditions in accordance with respective distances were used. In addition, the sensitivity of the sensor was adjusted in accordance with the amount of light.

Measurement was performed for 60 seconds at a sampling frequency of 500 Hz, and analysis was performed off-line. The sampling was obtained by using an analog front-end (AFE) "AFE4403EVM" (made by Texas Instruments Incorporated). Calculation of AC/DC is as described below, and was calculated by taking an average of ten measurements for each of the back of an arm side, a wrist ulna side, a wrist radius side, the abdomen, and the chest.

For the circuit side, a bandpass filter and a low-pass filter were used. For data processing, a moving average and the frequency-domain method were used.

In addition, it was assumed that the thickness t of the skin (epidermis+dermis) of a human body on the back of an arm side where the sensor was worn was 4 (mm), the thickness t of the skin of a human body at a wrist ulna side was 3.5 (mm), the thickness t of the skin of a human body at a wrist radius side was 3 (mm), the thickness t of the skin of a human body at the abdomen was 2.5 (mm), and the thickness t of the human body at the chest was 2 (mm).

<Regarding AC/DC>

As described in "<Method of calculating oxygen saturation>" above, the AC component of absorbance is specified by calculating the difference between the maximum value and minimum value of the change over time of the absorbance, and the DC component of the absorbance is specified by calculating an average of the change over time of the absorbance. The AC/DC value is calculated in accordance with (AC component of absorbance)/(DC component of absorbance) and indicated in the following Table I and Table II.

In the present invention, it was assumed that the fluctuation of the AC/DC value being in a range of 0.20% is desirable for practical use, and in particular being greater than or equal to 0.30% is desirable. In addition, it was assumed that, in light of the size of the device, being less than or equal to 0.80% is desirable for practical use.

TABLE I

| | Wearing site | Skin thickness of living body (mm) | Photoplethysmogram sensor No. | Minimum distance between light emitting element and light receiving element | Is Expression (1) satisfied? | Average AC/DC (%) |
|---|---|---|---|---|---|---|
| Comparative example 1 | Back of arm side | 4 | 1 | 2.5 | N | 0.02 |
| Comparative example 2 | Back of arm side | 4 | 2 | 5 | N | 0.06 |
| Comparative example 3 | Back of arm side | 4 | 3 | 7.5 | N | 0.12 |
| Example 1 | Back of arm side | 4 | 4 | 10 | Y | 0.20 |
| Example 2 | Back of arm side | 4 | 5 | 12.5 | Y | 0.26 |
| Example 3 | Back of arm side | 4 | 6 | 15 | Y | 0.33 |
| Example 4 | Back of arm side | 4 | 7 | 17.5 | Y | 0.39 |
| Example 5 | Back of arm side | 4 | 8 | 20 | Y | 0.44 |
| Example 6 | Back of arm side | 4 | 9 | 22.5 | Y | 0.49 |
| Example 7 | Back of arm side | 4 | 10 | 25 | Y | 0.50 |
| Comparative example 4 | Wrist ulna side | 3.5 | 1 | 2.5 | N | 0.06 |
| Comparative example 5 | Wrist ulna side | 3.5 | 2 | 5 | N | 0.12 |
| Example 8 | Wrist ulna side | 3.5 | 3 | 7.5 | Y | 0.22 |
| Example 9 | Wrist ulna side | 3.5 | 4 | 10 | Y | 0.35 |

TABLE I-continued

| | Wearing site | Skin thickness of living body (mm) | Photoplethysmogram sensor No. | Minimum distance between light emitting element and light receiving element | Is Expression (1) satisfied? | Average AC/DC (%) |
|---|---|---|---|---|---|---|
| Example 10 | Wrist ulna side | 3.5 | 5 | 12.5 | Y | 0.49 |
| Example 11 | Wrist ulna side | 3.5 | 6 | 15 | Y | 0.58 |
| Example 12 | Wrist ulna side | 3.5 | 7 | 17.5 | Y | 0.68 |
| Example 13 | Wrist ulna side | 3.5 | 8 | 20 | Y | 0.73 |
| Comparative example 6 | Wrist radius side | 3 | 1 | 2.5 | N | 0.10 |
| Example 14 | Wrist radius side | 3 | 2 | 5 | Y | 0.20 |
| Example 15 | Wrist radius side | 3 | 3 | 7.5 | Y | 0.36 |
| Example 16 | Wrist radius side | 3 | 4 | 10 | Y | 0.54 |
| Example 17 | Wrist radius side | 3 | 5 | 12.5 | Y | 0.66 |
| Example 18 | Wrist radius side | 3 | 6 | 15 | Y | 0.80 |
| Comparative example 7 | Wrist radius side | 3 | 7 | 17.5 | N | 0.91 |
| Comparative example 8 | Wrist radius side | 3 | 8 | 20 | N | 0.98 |

TABLE II

| | Wearing site | Skin thickness of living body (mm) | Photoplethysmogram sensor No. | Minimum distance between light emitting element and light receiving element | Is expression (1) satisfied? | Average AC/DC (%) |
|---|---|---|---|---|---|---|
| Comparative example 9 | Abdomen | 2.5 | 1 | 2.5 | N | 0.19 |
| Example 19 | Abdomen | 2.5 | 2 | 5 | Y | 0.38 |
| Example 20 | Abdomen | 2.5 | 3 | 7.5 | Y | 0.60 |
| Example 21 | Abdomen | 2.5 | 4 | 10 | Y | 0.79 |
| Comparative example 10 | Abdomen | 2.5 | 5 | 12.5 | N | 0.94 |
| Comparative example 11 | Abdomen | 2.5 | 6 | 15 | N | 1.10 |
| Comparative example 12 | Abdomen | 2.5 | 7 | 17.5 | N | 1.20 |
| Comparative example 13 | Abdomen | 2.5 | 8 | 20 | N | 1.24 |
| Example 22 | Chest | 2 | 11 | 2 | Y | 0.23 |
| Example 23 | Chest | 2 | 1 | 2.5 | Y | 0.32 |
| Example 24 | Chest | 2 | 2 | 5 | Y | 0.52 |
| Comparative example 14 | Chest | 2 | 3 | 7.5 | N | 0.81 |
| Comparative example 15 | Chest | 2 | 4 | 10 | N | 0.96 |
| Comparative example 16 | Chest | 2 | 5 | 12.5 | N | 1.11 |
| Comparative example 17 | Chest | 2 | 6 | 15 | N | 1.24 |
| Comparative example 18 | Chest | 2 | 7 | 17.5 | N | 1.34 |
| Comparative example 19 | Chest | 2 | 8 | 20 | N | 1.40 |

As indicated by the above results, that the AC/DC value increases in accordance with increasing the minimum distance h can be confirmed. However, when the minimum distance h is increased too much, an attenuation effect on the amount of light increases and the power consumption increases, and there is also is a greater likelihood of the signal strength decreasing and being affected by noise.

Accordingly, in comparison to a reflective photoplethysmogram sensor of a comparative example, a reflective photoplethysmogram sensor according to the present invention that satisfies the abovementioned Expression (1) does not undergo a reduction an attenuation effect for the amount of light, does not have an increase in power consumption, and also does not suffer a decrease in the signal strength and is less likely to be affected by noise. Accordingly, it is found that a reflective photoplethysmogram sensor according to the present invention is superior in measurement accuracy.

In accordance with the abovementioned means of the present embodiment, it is possible to provide a reflective photoplethysmogram sensor and a biological information measurement apparatus that can achieve both wearability and measurement accuracy.

The mechanism of expression or mechanism of action for effects of the present embodiment are not clarified, but on the basis of findings as follows, it is considered that the object according to the present invention was solved.

From academic research, it is known that, when light is irradiated onto a biological tissue which is a strong scatterer, the irradiated light propagates by expanding from the irradiation point into a hemispherical shape within the scatterer, but the propagation path of detected light has a banana shape.

In the present embodiment, envisioning phenomena such as the above, by carrying out various trial-and-error experiments and examinations, when the thickness of the skin (epidermis+dermis) of a human body is assumed to be in a range of 0.1-4 mm and the light emitting element and light receiving element do not face each other in the up/down direction, that is the two elements are disposed so as to not overlap, and when the reflective photoplethysmogram sensor is designed such that when the minimum distance between the light emitting element and the light receiving element is in a range that satisfies the Expression (1), being able to suppress measurement variation and being able to establish both of wearability and measurement accuracy was found.

As a result, expanding the measurement location is possible, and leading to constant monitoring or increased freedom for the measurement location is possible.

In addition, by having the photoplethysmogram sensor be of the reflective type, it is possible to expand the measurement location, and it is possible to realize a photoplethysmogram sensor that has little discomfort when worn.

Accordingly, the present embodiment contributes to improving measurement sensitivity and suppressing measurement variation for a reflective photoplethysmogram sensor.

Although embodiments of the present invention have been described and illustrated in detail, the disclosed embodiments are made for purposes of illustration and example only and not limitation. The scope of the present invention should be interpreted by terms of the appended claims

What is claimed is:

1. A biological information measurement apparatus comprising a controller and a reflective photoplethysmogram sensor, the reflective photoplethysmogram sensor comprising: a planar first light emitting element and a planar first light receiving element, wherein
   the first light emitting element and the first light receiving element do not face each other in an up/down direction, and
   a minimum distance h (mm) between at least a pair of the first light emitting element and the first light receiving element satisfies the following expression (1)

$$(t \times 0.7)^2 \leq h \leq (t \times 1.3)^2 \qquad \text{Expression (1):}$$

where the minimum distance between the first light emitting element and the first light receiving element is h (mm), and a thickness of skin (epidermis+dermis) of a human body is t (mm), and the thickness is within the range 0.1 to 4 mm,
   the first light emitting element or the first light receiving element comprises an arc shape,
   the reflective photoplethysmogram sensor further comprises a second light emitting element or a second light receiving element so,
   when the second light emitting element is provided, each of the first and second light emitting elements is arranged in the arc shape with a center point of the first light receiving element as a center, the controller is configured to subtract data obtained based on light emitted from the second light emitting element that does not satisfy the Expression (1) with the first light receiving element from data obtained based on light emitted from the first light emitting element that sataisfies the Expression (1) to remove a noise, and
   when the second light receiving elements are provided, each of the first and second light receiving elements is arranged in the arc shape with a center point of the first light emitting element as a center, and the controller is configured to subtract data obtained based on light received from the second light receiving element that does not satisfy the Expression (1) with the first light emitting element from data obtained based on light received from the first light receiving element that satisfies the Expression (1) to remove the noise.

2. The biological information measurement apparatus according to claim 1, wherein the minimum distance between the first light emitting element and the first light receiving element is in the range of 2 to 25 mm.

3. The biological information measurement apparatus according to claim 1, wherein the first light emitting element is an organic EL diode.

4. The biological information measurement apparatus according to claim 1, wherein the first light receiving element is an organic photodiode.

5. The biological information measurement apparatus according to claim 1, wherein
   the reflective photoplethysmogram sensor comprises the first and second light emitting elements, and
   the first and second light emitting elements are respectively disposed on approximately concentric circles centered on the center point of the first light receiving element.

6. The biological information measurement apparatus according to claim 1, wherein
   the reflective photoplethysmogram sensor comprises a plurality of light emitting elements including the first and second light emitting elements,
   at least two light emitting elements among the plurality of light emitting elements radiate light of a same wavelength, and each of the plurality of light emitting elements can emit light individually.

7. The biological information measurement apparatus according to claim 6, wherein processing is performed on information/data obtained on the basis of light respectively emitted by, among the plurality of light emitting elements, the second light emitting element disposed at a position close to the first light receiving element and the first light emitting element disposed at a position farther away from the first light receiving element than the second light emitting element.

8. The biological information measurement apparatus according to claim 1, wherein
the reflective photoplethysmogram sensor comprises a plurality of light receiving elements including the first and second light receiving elements, and
the plurality of light receiving elements is respectively disposed on approximately concentric circles centered on the center point of the first light emitting element.

9. The biological information measurement apparatus according to claim 8, wherein processing is performed on information/data obtained on the basis of light respectively received by, among the plurality of light receiving elements, the second light receiving element disposed at a position close to the first light emitting element and the first light receiving element disposed at a position farther away from the first light emitting element than the second light receiving element.

* * * * *